US011213397B2

(12) United States Patent
Wainscott et al.

(10) Patent No.: US 11,213,397 B2
(45) Date of Patent: Jan. 4, 2022

(54) PROSTHESIS WITH SURFACES HAVING DIFFERENT TEXTURES AND METHOD OF MAKING THE PROSTHESIS

(71) Applicant: DEPUY IRELAND UNLIMITED COMPANY, Cork (IE)

(72) Inventors: Stephanie M. Wainscott, Warsaw, IN (US); Daren L. Deffenbaugh, Winona Lake, IN (US); Hengda D. Liu, Warsaw, IN (US); Andrew J. Martin, Carmel, NY (US); Jeffrey A. Rybolt, Fort Wayne, IN (US); Bryan J. Smith, Fort Wayne, IN (US); Anthony D. Zannis, Dublin, CA (US)

(73) Assignee: DEPUY IRELAND UNLIMITED COMPANY, Loughbeg Industrial Estate (IE)

( * ) Notice: Subject to any disclaimer, the term of this patent is extended or adjusted under 35 U.S.C. 154(b) by 160 days.

(21) Appl. No.: 16/534,287

(22) Filed: Aug. 7, 2019

(65) Prior Publication Data
US 2019/0358041 A1 Nov. 28, 2019

Related U.S. Application Data

(60) Continuation of application No. 15/589,216, filed on May 8, 2017, now Pat. No. 10,433,964, which is a
(Continued)

(51) Int. Cl.
*A61F 2/38* (2006.01)
*A61F 2/30* (2006.01)
(Continued)

(52) U.S. Cl.
CPC .......... *A61F 2/30734* (2013.01); *A61F 2/38* (2013.01); *A61F 2/389* (2013.01); *A61F 2/4202* (2013.01);
(Continued)

(58) Field of Classification Search
CPC ....................... A61F 2/389; A61F 2002/30878
See application file for complete search history.

(56) References Cited

U.S. PATENT DOCUMENTS 3,852,045 A 12/1974 Wheeler et al.
3,855,638 A 12/1974 Pilliar
(Continued)

FOREIGN PATENT DOCUMENTS

CN 1889896 A 1/2007
CN 201200500 Y 3/2009
(Continued)

OTHER PUBLICATIONS

Chinese Search Report for Corresponding Chinese Application No. CN200980119036.9 dated Apr. 8, 2014, 2 Pages.
(Continued)

*Primary Examiner* — Suba Ganesan

(57) ABSTRACT

A joint prosthesis system is suitable for cementless fixation. The system includes a metal implant component that has a mounting surface for supporting an insert. The metal implant component includes a solid metal portion and a porous metal portion. The porous metal portion has surfaces with different characteristics, such as roughness, to improve bone fixation, ease removal of the implant component in a revision surgery, reduce soft tissue irritation, improve the strength of a sintered bond between the solid and porous metal portions, or reduce or eliminate the possibility of blood traveling through the porous metal portion into the joint space. A method of making the joint prosthesis is also disclosed. The invention may also be applied to discrete porous metal implant components, such as augment.

16 Claims, 29 Drawing Sheets

Related U.S. Application Data division of application No. 14/794,926, filed on Jul. 9, 2015, now abandoned, which is a division of application No. 12/904,578, filed on Oct. 14, 2010, now Pat. No. 9,101,476, which is a continuation-in-part of application No. 12/470,397, filed on May 21, 2009, now Pat. No. 8,871,142.

(60) Provisional application No. 61/256,468, filed on Oct. 30, 2009.

(51) Int. Cl.

| | | |
|---|---|---|
| *A61F 2/42* | (2006.01) | |
| *A61L 27/04* | (2006.01) | |
| *A61L 27/06* | (2006.01) | |
| *A61L 27/50* | (2006.01) | |
| *A61L 27/56* | (2006.01) | |
| *B22F 3/11* | (2006.01) | |
| *B22F 7/00* | (2006.01) | |
| *C22C 14/00* | (2006.01) | |
| *C22C 19/07* | (2006.01) | |
| *C22C 27/02* | (2006.01) | |
| *B22F 1/00* | (2006.01) | |
| *B22F 3/24* | (2006.01) | |

(52) U.S. Cl.
CPC ............ *A61L 27/04* (2013.01); *A61L 27/06* (2013.01); *A61L 27/50* (2013.01); *A61L 27/56* (2013.01); *B22F 1/0003* (2013.01); *B22F 3/1121* (2013.01); *B22F 3/1125* (2013.01); *B22F 3/1134* (2013.01); *B22F 3/1146* (2013.01); *B22F 3/24* (2013.01); *B22F 7/006* (2013.01); *C22C 14/00* (2013.01); *C22C 19/07* (2013.01); *C22C 27/02* (2013.01); *A61F 2002/30011* (2013.01); *A61F 2002/3092* (2013.01); *A61F 2002/30604* (2013.01); *A61F 2002/30878* (2013.01); *A61F 2002/30968* (2013.01); *A61F 2310/00023* (2013.01); *A61L 2400/18* (2013.01); *B22F 2003/247* (2013.01); *B22F 2301/205* (2013.01); *B22F 2998/10* (2013.01)

(56) References Cited

U.S. PATENT DOCUMENTS

| | | |
|---|---|---|
| 4,156,943 A | 6/1979 | Collier |
| 4,206,516 A | 6/1980 | Pilliar |
| 4,479,271 A * | 10/1984 | Bolesky ............ A61F 2/30907 623/20.17 |
| 4,550,448 A | 11/1985 | Kenna |
| 4,612,160 A | 9/1986 | Donlevy |
| 4,944,760 A | 7/1990 | Kenna |
| 4,954,170 A | 9/1990 | Fey |
| 4,969,904 A | 11/1990 | Koch |
| 5,019,103 A | 5/1991 | Van Zile et al. |
| 5,104,410 A | 4/1992 | Chowdhary |
| 5,201,766 A | 4/1993 | Georgette |
| 5,251,468 A | 10/1993 | Lin et al. |
| 5,282,861 A | 2/1994 | Kaplan |
| 5,308,556 A | 5/1994 | Bagley |
| 5,344,494 A | 9/1994 | Davidson et al. |
| 5,368,881 A | 11/1994 | Kelman |
| 5,605,491 A | 2/1997 | Yam |
| 5,658,333 A | 8/1997 | Kelman |
| 5,728,748 A | 3/1998 | Sun |
| 5,732,469 A | 3/1998 | Hamamoto |
| 5,765,095 A | 6/1998 | Flak et al. |
| 5,766,257 A | 6/1998 | Goodman |
| 5,989,027 A | 1/1999 | Meeks et al. |
| 5,879,400 A | 3/1999 | Merrill |
| 5,984,969 A | 11/1999 | Matthews |
| 6,005,018 A | 12/1999 | Cicierega |
| 6,017,975 A | 1/2000 | Saum |
| 6,042,780 A | 3/2000 | Huang |
| 6,123,896 A | 9/2000 | Meeks, III et al. |
| 6,135,857 A | 10/2000 | Shaw et al. |
| 6,165,223 A | 12/2000 | Metzger |
| 6,228,900 B1 | 5/2001 | Shen |
| 6,242,507 B1 | 6/2001 | Saum |
| 6,245,276 B1 | 6/2001 | McNulty |
| 6,281,264 B1 | 8/2001 | Salovey |
| 6,316,158 B1 | 11/2001 | Saum |
| 6,416,552 B1 | 7/2002 | Hoeppner |
| 6,524,522 B2 | 2/2003 | Vaidyanathan et al. |
| 6,582,470 B1 | 6/2003 | Lee et al. |
| 6,592,787 B2 | 7/2003 | Pickrell et al. |
| 6,660,224 B2 | 12/2003 | Lefebvre et al. |
| 6,846,327 B2 | 1/2005 | Khandkar et al. |
| 6,849,230 B1 | 2/2005 | Feichtinger |
| 6,852,272 B2 | 2/2005 | Artz et al. |
| 6,974,482 B2 | 12/2005 | Zhu et al. |
| 7,018,418 B2 | 3/2006 | Amrich et al. |
| 7,018,583 B2 | 3/2006 | Berger et al. |
| 7,147,819 B2 | 12/2006 | Bram et al. |
| 7,175,665 B2 | 2/2007 | German et al. |
| 7,628,818 B2 | 12/2009 | Hazebrouck et al. |
| 7,714,927 B2 | 5/2010 | Terashima |
| 7,875,083 B2 | 1/2011 | Sudmann |
| 8,163,027 B2 | 4/2012 | Rhodes et al. |
| 8,187,335 B2 | 5/2012 | Wyss |
| 8,192,498 B2 | 6/2012 | Wagner |
| 8,206,451 B2 | 6/2012 | Wyss |
| 8,236,061 B2 | 8/2012 | Heldreth |
| 8,308,300 B2 | 11/2012 | Sudo |
| 8,419,800 B2 | 4/2013 | Tuke |
| 8,470,047 B2 | 6/2013 | Hazebrouck |
| 8,658,710 B2 | 2/2014 | Mckellop |
| 8,796,347 B2 | 8/2014 | Mckellop |
| 8,828,086 B2 | 9/2014 | Williams |
| 8,871,142 B2 | 10/2014 | Smith |
| 9,101,476 B2 | 8/2015 | Deruntz et al. |
| 2003/0035747 A1 | 2/2003 | Anderson et al. |
| 2003/0044301 A1 | 3/2003 | Lefebvre et al. |
| 2003/0075013 A1 | 4/2003 | Grohowski |
| 2003/0153981 A1 | 8/2003 | Wang |
| 2004/0167633 A1 | 8/2004 | Wen et al. |
| 2005/0100578 A1 | 5/2005 | Schmid et al. |
| 2005/0112397 A1 | 5/2005 | Rolfe |
| 2005/0249625 A1 | 11/2005 | Bram et al. |
| 2006/0002810 A1 | 1/2006 | Grohowski, Jr. |
| 2006/0163774 A1 | 7/2006 | Abels et al. |
| 2006/0178749 A1 | 8/2006 | Pendleton et al. |
| 2006/0228247 A1 | 10/2006 | Grohowski |
| 2006/0241781 A1 | 10/2006 | Brown |
| 2006/0246397 A1 | 11/2006 | Wolf |
| 2006/0257358 A1 | 11/2006 | Wen |
| 2007/0172380 A1 | 7/2007 | Tatsumoto et al. |
| 2007/0173948 A1 | 7/2007 | Meridew et al. |
| 2007/0196230 A1 | 8/2007 | Hamman et al. |
| 2007/0255412 A1* | 11/2007 | Hajaj ............ A61F 2/38 623/17.11 |
| 2008/0147187 A1 | 6/2008 | Bollinger et al. |
| 2008/0199720 A1 | 8/2008 | Liu et al. |
| 2008/0215098 A1 | 9/2008 | Imwinkelried et al. |
| 2008/0288083 A1 | 11/2008 | Axelsson |
| 2009/0292365 A1 | 11/2009 | Smith et al. |
| 2009/0326674 A1 | 12/2009 | Liu et al. |
| 2010/0098574 A1 | 4/2010 | Liu |
| 2011/0009974 A1 | 1/2011 | Blaylock et al. |

FOREIGN PATENT DOCUMENTS

| | | |
|---|---|---|
| EP | 1779812 A1 | 5/2007 |
| JP | 62205201 A | 9/1987 |
| JP | 2007075485 | 3/2007 |
| WO | 2003101647 A2 | 12/2003 |
| WO | 2005009489 A2 | 2/2005 |
| WO | 2005009729 A2 | 2/2005 |
| WO | 2006014294 A1 | 2/2006 |

(56) References Cited

FOREIGN PATENT DOCUMENTS

| WO | 2006079459 | A1 | 8/2006 |
|---|---|---|---|
| WO | 2006130350 | A2 | 12/2006 |
| WO | 2007090529 | A1 | 8/2007 |
| WO | 2009143420 | | 11/2009 |

OTHER PUBLICATIONS

Bram, M., et al "High Porosity Titanium, Stainless Steel and Superalloy Parts," Adv. Eng. Mat. 2000 2(4), 196-199.
Laptev, A., et al "Green Strength of Powder Compacts Provided for Production of Highly Porous Titanium Parts, Powder Metallurgy." 2005 48(4), 358-364.
Wen, C.E., et al "Fabrication & Characterization of Autogenous Tatnium Foams." Eur. Cells and Mat. 2001 vol. 1 (Suppl. 2) 61-62.
Wen, C.E., et al "Processing of Biocompatible Porous Ti And Mg." Scripta Materialia 45 (2001) 1147-1153.
Zhao, et al, "A Novel Sintering-Dissolution Process for Manufacturing Al Foams." Scripta Materialia 44 (2001) 105-110.
Zhao, et al "Optimisation of Compaction and Liquid-State Sintering in Sintering and Dissolution Process for Manufacturing Al Foams." Materials Science & Eingeering, Jul. 30, 2003, A 364, pp. 117-125.
Carl Zeiss, Zeiss Surfcomm 5000 "Contour and Surface Measuring Machines." 2005, 16 Pages.
Phelly Materials, Inc. "Hybride and Dehydride CP Ti and Ti-6A1-4V Powders." 2007, 1 Page.
Phelly Materials, Inc., "Pure Metal Powder." 2007, 1 Page.
International Standard ISO 4287:1997; Geometrical Product Specifications (GPS)—Surface Texture: Profile Method—Terms, Definitons and Surface Texture Parameters, 1997, 36 Pages.
International Standard ISO 4287:1997; Geometrical Product Specifications (GPS)—Surface Texture: Profile Method—Terms, Definitions and Surface Texture Parameters, Technical Corrigendum 1, 1998, 2 Pages.
International Standard ISO 4287:1997; Geometrical Product Specifications (GPS)—Surface Fexture: Profile Method—Terms, Definitions and Surface Texture Parameters, Technical Corrigendum 2, 2005, 2 Pages.

Bozkaya, D., et al: "Mechanics of the Taper Integrated Screw-In (TIS) Abutments Used in Dental Implants." Journal of Biomechanics, vol. 38, No. 1, Jan. 1, 2005, pp. 87-97, XP027738016.
Grant, J.A., et al: "Artificial Composite Bone as a Model of Human Trabecular Bone: the Implant-Bone Interface." Journal of Biomechanics vol. 40, No. 5, Jan. 1, 2007, pp. 1158-1164 (XP055073219).
German, R.: "Powder Injection Molding." ASM Handbook, vol. 7 (1998), pp. 355-364 (Examiner Citation in US Publication No. 20090292365).
Wen, C.E., et al: "Novel Titanium-Foam for Bone Tissue Engineering." Journal of Materials Research, vol. 17, No. 10, pp. 2633-2639 (Oct. 2002).
PCT International Search Report for Application No. PCT/US2011/056111 dated Jan. 25, 2012, 6 Pages.
PCT International Search Report for Application No. PCT/US2009/044970 dated Jul. 29, 2010, 21 Pages.
Japanese Search Report for Japanese Patent App. No. JP2013-533999 dated Aug. 24, 2015, 5 Pages.
Chinese Search Report for Chinese Patent App. No. 201180059783.5 dated Dec. 7, 2014, 2 Pages.
Chinese Search Report for Chinese Patent App. No. 201010538300.7 dated Mar. 26, 2014, 3 Pages.
Shen Xin, Introduction on Foreign Surface Roughness Standard, Aeronautic Standardization and Quality No. 5, Published Oct. 28, 1982, 12 Pages (English Translation Not Available).
Japanese Search Report for Japanese App. No. JP2010-243349 dated Mar. 10, 2015, 3 Pages.
Berend, et al "Effects of Coronal Plane Conformity on Tibial Loading in TKA: a Comparison of AGC Flat Versus Conforming Articulations." (Surgical Technology Int., No. 18, pp. 207-212, 2009.
Chinese Search Report for Chinese App. No. CN201610181519.3 dated Mar. 27, 2017, 3 Pages.
European Search Report for Epo App. No. 14153861.1-1654 dated Mar. 11, 2014, 7 Pages.
Indian Search Report for Indian Application No. 1183/KOL/2010 dated Dec. 17, 2018, 6 Pages.

\* cited by examiner

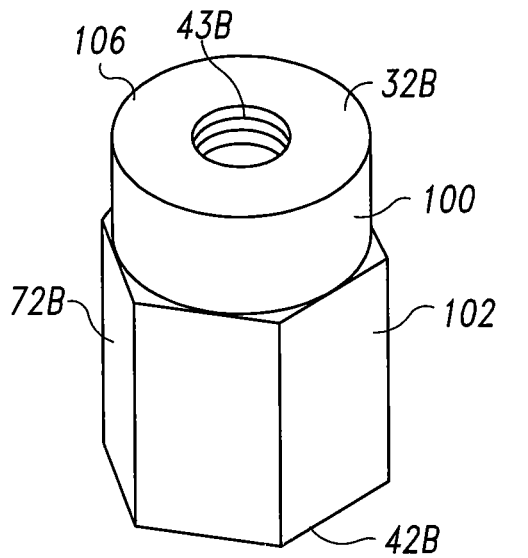 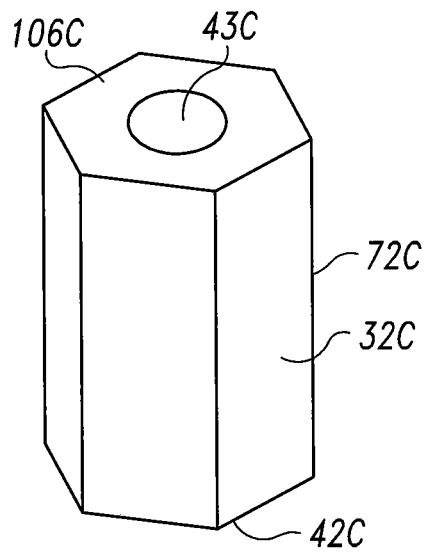
Fig. 12        Fig. 13
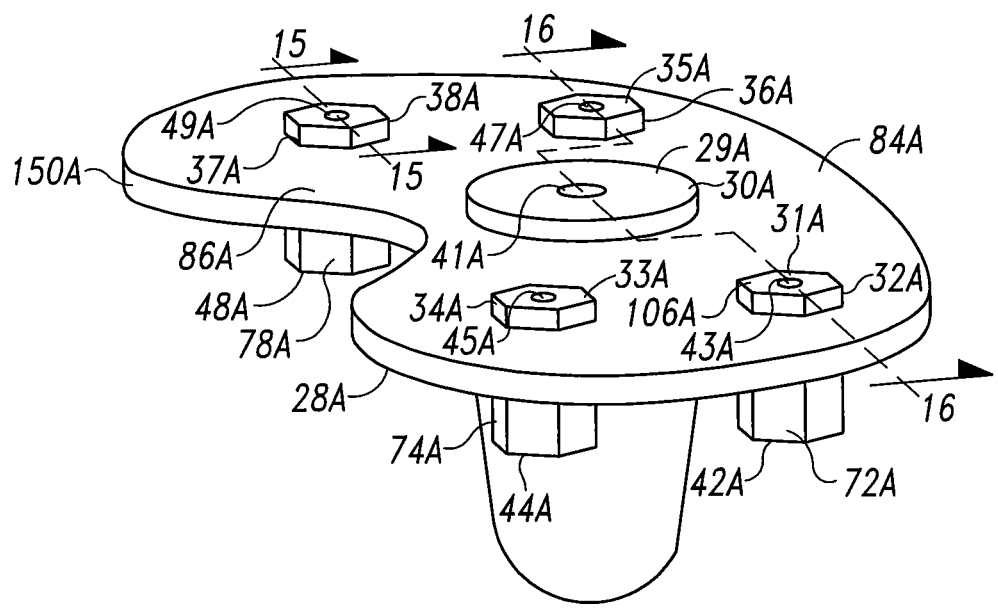
Fig. 14

FIG. 33A

| Green Machined Samples – Surface Profile Parameters | | | | | | | | | | |
|---|---|---|---|---|---|---|---|---|---|---|
| Sample | Pa | Pq | Pp | Pv | Pc.I | PSm | PDq | Psk | Pku | Pt |
| 1 | 21.26 | 26.06 | 51.55 | 75.69 | 72.56 | 2570.48 | 0.17 | -0.38 | 2.73 | 127.24 |
| 2 | 16.44 | 20.46 | 36.91 | 57.71 | 69.5 | 2235.42 | 0.16 | -0.64 | 2.86 | 94.62 |
| 3 | 15.12 | 18.64 | 46.7 | 54.34 | 60.94 | 1697.81 | 0.16 | -0.09 | 2.75 | 101.04 |
| 4 | 15.03 | 18.49 | 34.48 | 52.05 | 49.67 | 1311.73 | 0.17 | -0.33 | 2.64 | 86.53 |
| 5 | 13.01 | 16.46 | 33.6 | 55.83 | 50.27 | 1217.69 | 0.16 | -0.5 | 3.17 | 89.44 |
| 6 | 13.54 | 18.16 | 58.68 | 59.08 | 58.37 | 2257.42 | 0.16 | 0 | 3.97 | 117.76 |
| 7 | 15.12 | 19.9 | 54.11 | 63.58 | 62.9 | 2124.47 | 0.15 | -0.13 | 3.37 | 117.69 |
| 8 | 14.38 | 18.04 | 36.95 | 59.23 | 76.44 | 2813.93 | 0.15 | -0.44 | 3 | 96.19 |
| 9 | 37.43 | 55.87 | 66.03 | 223.32 | 194.1 | 6994.23 | 0.18 | -1.98 | 6.76 | 289.35 |
| 10 | 25.08 | 32.9 | 71.28 | 100.76 | 79.56 | 1535.94 | 0.18 | -0.73 | 3.58 | 172.04 |
| Group 1 Average | 18.64 | 24.5 | 49.03 | 80.16 | 77.43 | 2475.91 | 0.16 | -0.52 | 3.48 | 129.19 |
| Group 1 St Dev | 7.6 | 12.07 | 13.57 | 52.33 | 42.24 | 1673.15 | 0.01 | 0.57 | 1.23 | 61.67 |
| 11 | 14.8 | 18.8 | 41.8 | 49.7 | 47.9 | 1734.5 | 0.1 | -0.3 | 2.8 | -- |
| 12 | 11.5 | 14.8 | 20.8 | 47.3 | 39.0 | 897.8 | 0.2 | -1.2 | 3.8 | -- |
| Group 2 Average | 13.15 | 16.8 | 31.3 | 48.5 | 43.45 | 1316.15 | 0.15 | -0.75 | 3.3 | |
| Overall Average | 17.73 | 23.22 | 46.07 | 74.88 | 71.77 | 2282.62 | 0.16 | -0.56 | 3.45 | 129.19 |

FIG. 33B

| Green Machined Samples – Surface Roughness Parameters | | | | | | |
|---|---|---|---|---|---|---|
| Sample | Ra | Rz | Rp | Rpmax | Rv | Rt |
| 11 | 6.2 | 26.5 | 10.1 | 12.4 | 16.3 | 32.6 |
| 12 | 5.9 | 28.0 | 10.2 | 16.2 | 17.8 | 44.3 |
| Group 2 Average | 6.05 | 27.25 | 10.15 | 14.3 | 17.05 | 38.45 |

FIG. 34A

Salt Blasted Samples – Surface Profile Parameters

| Sample | Pa | Pq | Pp | Pv | Pc.I | PSm | PDq | Psk | Pku |
|---|---|---|---|---|---|---|---|---|---|
| 1 | 94.24 | 118.87 | 191.5 | 341.1 | 340.27 | 2271.05 | 0.53 | -0.54 | 2.85 |
| 2 | 86.45 | 112.63 | 209.94 | 320.92 | 307.18 | 1928.79 | 0.46 | -0.64 | 3.05 |
| 3 | 91.28 | 112.14 | 216.33 | 270.26 | 339.09 | 4117.21 | 0.4 | -0.11 | 2.51 |
| 4 | 74.06 | 98.97 | 221.11 | 401.18 | 291.99 | 2394.15 | 0.46 | -0.67 | 4.73 |
| 5 | 68.26 | 85.39 | 213.92 | 188.88 | 239.74 | 1743.64 | 0.43 | 0.35 | 2.63 |
| Group 1 Average | 82.86 | 105.60 | 210.56 | 304.47 | 303.65 | 2490.97 | 0.46 | -0.32 | 3.15 |
| 6 | 84.5 | 110.2 | 160.9 | 407.4 | 313.2 | 1707.4 | 0.4 | -1.1 | 5.0 |
| 7 | 78.4 | 98.1 | 155.2 | 334.2 | 372.1 | 2797.7 | 0.5 | -0.9 | 3.8 |
| Group 2 Average | 81.45 | 104.15 | 158.05 | 370.80 | 342.65 | 2252.55 | 0.45 | -1.00 | 4.40 |
| Overall Average | 82.46 | 105.19 | 195.56 | 323.42 | 314.8 | 2422.85 | 0.45 | -0.52 | 3.51 |

FIG. 34B

Salt Blasted Samples – Surface Roughness Parameters

| Sample | Ra | Rz | Rp | Rpmax | Rv | Rt |
|---|---|---|---|---|---|---|
| 6 | 16.4 | 71.0 | 20.7 | 29.0 | 50.3 | 111.4 |
| 7 | 16.5 | 74.5 | 18.9 | 30.8 | 55.6 | 180.8 |
| Average | 16.45 | 72.75 | 19.8 | 29.9 | 52.95 | 146.1 |

FIG. 35A

| Milled Surface Samples - Surface Profile Parameters | | | | | | | | | | |
|---|---|---|---|---|---|---|---|---|---|---|
| Sample | Pa | Pq | Pp | Pv | Pc.I | PSm | PDq | Psk | Pku |
| 1 | 4.80 | 6 | 15 | 16.90 | 18.44 | 2480.88 | 0.06 | 0.29 | 2.65 |
| 2 | 4.83 | 6.18 | 16.52 | 16.54 | 16 | 3381.19 | 0.05 | 0.52 | 3.15 |
| 3 | 5.17 | 6.72 | 22.37 | 14.87 | 30.63 | 5243.54 | 0.06 | 0.73 | 3.57 |
| 4 | 4.07 | 5.46 | 17.53 | 17.05 | 18.73 | 2750.59 | 0.05 | 0.77 | 4.18 |
| 5 | 5.00 | 6.00 | 16.62 | 15.31 | 17.94 | 2283.06 | 0.05 | 0.31 | 2.31 |
| Group 1 Average | 4.77 | 6.07 | 17.61 | 16.13 | 20.35 | 3227.85 | 0.05 | 0.52 | 3.17 |
| 6 | 3.6 | 4.6 | 12.1 | 19.6 | 16.4 | 2089.4 | 0.1 | -0.6 | 4.1 |
| 7 | 2.7 | 3.6 | 10.2 | 10.5 | 12.4 | 1468.2 | 0.0 | 0.2 | 3.5 |
| Group 2 Average | 3.15 | 4.10 | 11.15 | 15.05 | 14.40 | 1778.80 | 0.05 | -0.20 | 3.80 |
| Overall Average | 4.31 | 5.51 | 15.76 | 15.82 | 18.65 | 2813.84 | 0.05 | 0.32 | 3.35 |

FIG. 35B

| Milled Surface Samples – Surface Roughness Parameters | | | | | | | |
|---|---|---|---|---|---|---|---|
| Sample | Ra | Rz | Rp | Rpmax | Rv | Rt |
| 6 | 2.2 | 12.4 | 4.6 | 10.7 | 7.8 | 26.9 |
| 7 | 2.5 | 14.1 | 4.8 | 7.6 | 9.3 | 23.5 |
| Average | 2.35 | 13.25 | 4.7 | 9.15 | 8.55 | 25.2 |

FIG. 36A

| Ground Surface Samples – Surface Profile Parameters |||||||||
|---|---|---|---|---|---|---|---|---|
| Sample | Pa | Pq | Pp | Pv | Pc.I | PSm | PDq | Psk | Pku |
| 1 | 2.8 | 4.1 | 17.2 | 16.6 | 15.6 | 770.5 | 0.1 | 0.6 | 6.7 |
| 2 | 3.6 | 5.1 | 11.3 | 21.4 | 19.5 | 1086.3 | 0.1 | -1.3 | 5.2 |
| Average | 3.2 | 4.6 | 14.3 | 19.0 | 17.5 | 928.4 | 0.1 | -0.3 | 5.9 |

FIG. 36B

| Ground Surface Samples – Surface Roughness Parameters ||||||
|---|---|---|---|---|---|
| Sample | Ra | Rz | Rp | Rpmax | Rv | Rt |
| 1 | 2.2 | 12.4 | 4.6 | 10.7 | 7.8 | 26.9 |
| 2 | 2.5 | 14.1 | 4.8 | 7.6 | 9.3 | 23.5 |
| Average | 2.4 | 13.3 | 4.7 | 9.2 | 8.6 | 25.2 |

FIG. 37A

| Turned on Research Lathe Samples – Surface Profile Parameters |||||||||
|---|---|---|---|---|---|---|---|---|
| Sample | Pa | Pq | Pp | Pv | Pc.I | PSm | PDq | Psk | Pku |
| 1 | 13.5 | 16.7 | 40.4 | 32.0 | 58.7 | 6348.6 | 0.1 | 0.4 | 2.5 |
| 2 | 12.6 | 16.2 | 44.7 | 30.3 | 62.1 | 4622.0 | 0.1 | 0.5 | 3.1 |
| Group 1 Average | 13.1 | 16.5 | 42.5 | 31.2 | 50.4 | 5485.3 | 0.1 | 0.5 | 2.8 |
| 3 | 10.3 | 12.0 | 23.6 | 21.5 | 37.4 | 3766.4 | 0.1 | 0.2 | 1.9 |
| 4 | 10.7 | 13.1 | 27.2 | 33.0 | 44.5 | 3322.0 | 0.1 | -0.2 | 2.4 |
| Group 2 Average | 10.5 | 12.6 | 25.4 | 27.3 | 40.9 | 3544.2 | 0.1 | 0.0 | 2.1 |
| Overall Average | 11.78 | 14.50 | 33.98 | 29.20 | 50.68 | 4514.75 | 0.10 | 0.23 | 2.48 |

FIG. 37B

| Turned on Research Lathe Samples – Surface Roughness Parameters ||||||
|---|---|---|---|---|---|
| Sample | Ra | Rz | Rp | Rpmax | Rv | Rt |
| 1 | 1.9 | 9.0 | 4.8 | 7.9 | 4.2 | 17.5 |
| 2 | 2.2 | 11.6 | 6.0 | 9.2 | 5.5 | 18.8 |
| Group 1 Average | 2.1 | 10.3 | 5.4 | 8.5 | 4.9 | 18.1 |
| 3 | 1.7 | 8.0 | 4.1 | 8.0 | 3.9 | 14.3 |
| 4 | 2.4 | 10.8 | 5.2 | 8.5 | 5.7 | 18.6 |
| Group 2 Average | 2.1 | 9.4 | 4.6 | 8.2 | 4.8 | 16.5 |
| Overall Average | | | | | | |

FIG. 38A

| Turned on Production Lathe Samples – Surface Profile Parameters | | | | | | | | | |
|---|---|---|---|---|---|---|---|---|---|
| Sample | Pa | Pq | Pp | Pv | Pc.I | PSm | PDq | Psk | Pku |
| 1 | 13.4 | 18.2 | 29.7 | 68.3 | 59.2 | 1864.7 | 0.1 | -1.8 | 6.4 |
| 2 | 10.4 | 15.5 | 30.9 | 58.3 | 43.7 | 1329.2 | 0.1 | -1.8 | 6.2 |
| Average | 11.0 | 16.9 | 30.3 | 63.3 | 51.5 | 1596.9 | 0.1 | -1.8 | 6.3 |

FIG. 38B

| Turned on Production Lathe Samples – Surface Roughness Parameters | | | | | | |
|---|---|---|---|---|---|---|
| Sample | Ra | Rz | Rp | Rpmax | Rv | Rt |
| 1 | 4.9 | 25.8 | 9.4 | 15.9 | 16.4 | 43.3 |
| 2 | 4.7 | 24.1 | 8.7 | 13.7 | 15.4 | 44.7 |
| Average | 4.8 | 24.9 | 9.0 | 14.8 | 15.9 | 44.0 |

FIG. 39

| Polished Samples | | | | | | | | | |
|---|---|---|---|---|---|---|---|---|---|
| Sample | Pa | Pq | Pp | Pv | Pc.I | PSm | PDq | Psk | Pku | Pt |
| 1 | 2.492758 | 3.361967 | 5.0948 | 18.9569 | 11.16668 | 847.2549 | 0.056562 | -1.62153 | 7.493695 | 24.0517 |
| 2 | 2.8826 | 3.807941 | 6.1326 | 16.6895 | 11.7986 | 648.424 | 0.05863 | -1.31256 | 5.125309 | 22.8221 |
| 3 | 3.130639 | 4.320033 | 5.2856 | 23.0231 | 13.12592 | 1064.356 | 0.056207 | -1.76333 | 6.800809 | 28.3087 |
| 4 | 3.599365 | 4.745303 | 7.4197 | 19.7501 | 14.85769 | 685.6344 | 0.068296 | -1.17823 | 4.702859 | 27.1698 |
| 5 | 5.178906 | 6.692851 | 9.7911 | 28.988 | 21.73534 | 1196.254 | 0.084064 | -1.04531 | 4.456093 | 38.7791 |
| Average | 3.456854 | 4.585619 | 6.74476 | 21.48152 | 14.53685 | 888.3847 | 0.064752 | -1.38419 | 5.715753 | 28.22628 |
| Std Dev | 1.043005 | 1.288271 | 1.934036 | 4.771234 | 4.265209 | 237.7657 | 0.011865 | 0.30103 | 1.350902 | 6.307084 |

PROSTHESIS WITH SURFACES HAVING DIFFERENT TEXTURES AND METHOD OF MAKING THE PROSTHESIS

The present application is a continuation of the following U.S. patent application Ser. No. 15/589,216, now U.S. Pat. No. 10,433,946, filed May 8, 2017, which is a divisional application of U.S. patent application Ser. No. 14/794,926, now abandoned, filed Jul. 9, 2015, which is a divisional application U.S. patent application Ser. No. 12/904,578, now U.S. Pat. No. 9,101,476, filed Oct. 14, 2010, which is a continuation-in-part of U.S. patent application Ser. No. 12/470,397, now U.S. Pat. No. 8,871,142, filed May 21, 2009, and which claims priority to U.S. Prov. App. Ser. No. 61/256,468, filed on Oct. 30, 2009, all of which are incorporated by reference herein in their entirety.

TECHNICAL FIELD

The present disclosure relates generally to implantable orthopaedic prostheses, and more particularly to implantable prostheses having bearing components and others component supporting the bearing components.

BACKGROUND

During the lifetime of a patient, it may be necessary to perform a joint replacement procedure on the patient as a result of, for example, disease or trauma. The joint replacement procedure may involve the use of a prosthesis that is implanted into one or more of the patient's bones. In the case of a knee replacement procedure, a tibial tray is implanted into the patient's tibia. A bearing is then secured to the tibial tray. The condyle surfaces of a replacement femoral component bear against the tibial bearing.

One type of knee prosthesis is a fixed-bearing knee prosthesis. As its name suggests, the bearing of a fixed-bearing knee prosthesis does not move relative to the tibial tray. Fixed-bearing designs are commonly used when the condition of the patient's soft tissue (i.e., knee ligaments) does not allow for the use of a knee prosthesis having a mobile bearing.

In contrast, in a mobile-bearing type of knee prosthesis, the bearing can move relative to the tibial tray. Mobile-bearing knee prostheses include so-called "rotating platform" knee prostheses, wherein the bearing can rotate about a longitudinal axis on the tibial tray.

Tibial trays are commonly made of a biocompatible metal, such as a cobalt chrome alloy or a titanium alloy.

For both fixed and mobile-bearing knee prostheses, the tibial trays may be designed to be cemented into place on the patient's tibia or alternatively may be designed for cementless fixation. Cemented fixation relies on mechanical bonds between the tibial tray and the cement as well as between the cement and the bone. Cementless implants generally have surface features that are conducive to bone ingrowth into the implant component and rely to a substantial part on this bony ingrowth for secondary fixation; primary fixation is achieved through the mechanical fit of the implant and the prepared bone.

Tibial components of both fixed and mobile-bearing and cemented and cementless knee arthroplasty systems are commonly modular components, comprising a tibial tray and a polymeric bearing carried by the tibial tray. The tibial trays commonly include features extending distally, such as pegs or stems. These extensions penetrate below the surface of the tibial plateau and stabilize the tibial tray component against movement. In cementless tibial implants, the outer surfaces of these extensions are typically porous to allow for bone ingrowth. For example, in the Zimmer Trabecular Metal Monoblock tibial trays, pegs with flat distal surfaces and hexagonal axial surfaces are formed completely of a porous metal. In such trays, bone ingrowth is likely to occur along all surfaces of the pegs, including the distal surfaces.

Femoral components of such knee prosthesis systems are also designed for either cemented or cementless fixation. For cemented fixation, the femoral component typically includes recesses or cement pockets. For cementless fixation, the femoral component is designed for primary fixation through a press-fit, and includes porous bone-engaging surfaces suitable for bone ingrowth. Both designs may include pegs designed to extend into prepared holes in the femur for stabilization of the implant.

On occasion, the primary knee prosthesis fails. Failure can result from many causes, including wear, aseptic loosening, osteolysis, ligamentous instability, arthrofibrosis and patellofemoral complications. When the failure is debilitating, revision surgery may be necessary. In a revision, the primary knee prosthesis (or parts of it) is removed and replaced with components of a revision prosthetic system.

When the tibial or femoral implant includes extensions (such as pegs or stems) that extend into the natural bone, a revision surgery usually requires a large resection of the bone in order to dislodge the extensions from the bone. This large resection not only complicates the surgery, it also requires removal of more of the patient's natural bone than is desirable. This removal of additional bone may further compromise the bone, increase the risk of onset of bone pathologies or abnormalities, or reduce the available healthy bone for fixation of the revision implant. Moreover, the large resection usually means that a larger orthopaedic implant is necessary to fill the space and restore the joint component to its expected geometry.

This difficulty in dislodging the primary implant components from the bones is worsened by the fact that bone also grows into the extensions. Severing these connections may be problematic since not all of these areas are easily accessible without resecting large amounts of bone.

In implants such as the Zimmer Trabecular Metal Monoblock tibia tray, some surfaces of the porous metal portion of the tibial tray may remain exposed above the tibial plateau after implantation. These exposed porous metal surfaces may be rough and may irritate the patient's soft tissue as the patient engages in normal day-to-day activities.

Similar issues may be presented in other types of joint prostheses.

SUMMARY

The present invention addresses the need for a prosthesis with a modular implant component suitable for cementless fixation that can be removed more readily from the bone in revision surgery to conserve native bone. In addition, the invention addresses the need for such an implant that minimizes soft tissue irritation. A method of making such a prosthesis is also disclosed, as well as a surgical method for removing such a prosthesis. While the illustrated embodiments of the invention address all of these needs, it should be understood that the scope of the invention as defined by the claims may include prostheses that address one or more of these needs. It should also be understood that various aspects of the present invention provide other additional advantages, as set forth more fully below. In addition, it should be understood that the principles of the present invention may be applied to knee prostheses as well as other joint prostheses, such as, for example, an ankle prosthesis.

In one aspect, the present invention provides an orthopaedic implant component comprising a porous metal body having a bone-engaging surface and a second surface extending from the bone-engaging surface. The bone-engaging surface has a static coefficient of friction and the second surface has a lower static coefficient of friction. The body has a void space of at least 60% by volume.

In another aspect, the present invention provides an orthopaedic implant component comprising a porous metal body having a bone-engaging surface and a second surface extending from the bone-engaging surface. The bone-engaging surface has a surface profile under ISO 4287 (1997) and the second surface has a different surface profile under ISO 4287 (1997). The body has a void space of at least 60% by volume.

In another aspect, the present invention provides an orthopaedic implant component comprising a porous metal body having a bone-engaging surface and a second surface extending from the bone-engaging surface. The bone-engaging surface has a surface roughness under ISO 4287 (1997) and the second surface has a lower surface roughness under ISO 4287 (1997). The body has a void space of at least 60% by volume.

In another aspect, the present invention provides an orthopaedic implant component comprising a porous metal body having a bone-engaging surface and a second surface extending from the bone-engaging surface. The bone-engaging surface has a surface porosity and the second surface has a lower surface porosity. The body has a void space of at least 60% by volume.

In each of the above aspects, an exemplary embodiment of the orthopaedic implant component may comprise a tibial tray having a solid metal portion. In this embodiment, the porous metal body is bonded to the solid metal portion and the bone-engaging surface of the porous metal body comprises the distal surface of the tibial tray. In this embodiment, the second surface extends around the periphery of the tibial tray and connects the solid metal portion to the bone-engaging surface of the body. In this embodiment, the second surface may include opposite portions and the porous metal body between the opposite portions of the second surface may comprise metal foam.

In each of the above aspects, an exemplary embodiment of the orthopaedic implant component comprises a tibial tray having a solid metal portion. The porous metal body in this embodiment comprises an extension extending distally from the tibial tray to a free distal end. In this embodiment, the free distal end of the extension defines the second surface of the porous metal body. In this embodiment, the extension may comprise a peg spaced from the central sagittal plane of the tibial tray or a stem positioned along the central sagittal plane of the tibial tray.

An exemplary embodiment of the orthopaedic implant component may also comprise a distal femoral component. In this embodiment, the implant component further includes a solid metal support portion, and the porous metal body may comprise an extension extending proximally from the tibial tray to a free proximal end. The free proximal end of the extension defines the second surface of the porous metal body. In this embodiment, the extension may comprise a peg spaced from the central sagittal plane of the distal femoral component.

In each of the above aspects, an exemplary embodiment of the orthopaedic implant component is part of an orthopaedic implant system that includes a second implant component having a bone-engaging surface. In this embodiment, the orthopaedic implant component comprises an augment configured to be selectively placed against the bone-engaging surface of the second implant component.

In another aspect, the present invention provides a method of making an orthopaedic implant component comprising obtaining a porous metal body having adjacent non-parallel surfaces. One of the adjacent non-parallel surfaces is roughened while the other non-parallel surface is machined without roughening.

In an exemplary embodiment, the step of roughening one of the adjacent non-parallel surfaces comprises salt blasting the surface.

In an exemplary embodiment, the method further comprises the step of sintering the porous metal body to a solid metal body.

In an exemplary embodiment, the porous metal body comprises metal foam having a void space of at least 60% by volume. The metal foam may comprise titanium foam.

In another aspect, the present invention provides a method of making an orthopaedic implant component comprising obtaining a porous metal body having adjacent non-parallel surfaces, each surface having a coefficient of static friction. One of the adjacent non-parallel surfaces is machined to lower the coefficient of static friction of that surface.

In an exemplary embodiment, one of the surfaces is roughened to increase the coefficient of static friction of the surface.

In an exemplary embodiment, the method further comprises the step of sintering the porous metal body to a solid metal body.

In an exemplary embodiment, the porous metal body comprises metal foam having a void space of at least 60% by volume. The metal foam may comprise titanium foam.

In another aspect, the present invention provides a method of making an orthopaedic implant component comprising obtaining a porous metal body having adjacent non-parallel surfaces, each surface having a surface profile. One of the adjacent non-parallel surfaces is machined to change the surface profile of that surface.

In an exemplary embodiment, one of the surfaces is roughened to change the surface profile of the roughened surface.

In an exemplary embodiment, the method further comprises the step of sintering the porous metal body to a solid metal body.

In an exemplary embodiment, the porous metal body comprises metal foam having a void space of at least 60% by volume. The metal foam may comprise titanium foam.

In another aspect, the present invention provides a method of making an orthopaedic implant component comprising obtaining a porous metal body having adjacent non-parallel surfaces. Each surface has a porosity. One of the adjacent non-parallel surfaces is machined to lower the porosity of that surface.

In an exemplary embodiment, one of the surfaces is roughened to increase the coefficient of static friction of the surface.

In an exemplary embodiment, the method further comprises the step of sintering the porous metal body to a solid metal body.

In an exemplary embodiment, the porous metal body comprises metal foam having a void space of at least 60% by volume. The metal foam may comprise titanium foam.

In another aspect, the present invention provides a method of making an orthopaedic implant component comprising obtaining a porous metal body having adjacent non-parallel surfaces, each surface having a roughness. One of the adjacent non-parallel surfaces is machined to lower the roughness of that surface.

In an exemplary embodiment, one of the surfaces is roughened to increase the roughness of the surface.

In an exemplary embodiment, the method further comprises the step of sintering the porous metal body to a solid metal body.

In an exemplary embodiment, the porous metal body comprises metal foam having a void space of at least 60% by volume. The metal foam may comprise titanium foam.

BRIEF DESCRIPTION OF THE DRAWINGS

The detailed description particularly refers to the following figures, in which:

FIG. 12 is a perspective view of an alternative form of peg that may be used for the tibial tray or femoral component;

FIG. 13 is a perspective view of another alternative form of peg that may be used for the tibial tray or femoral component;

FIG. 14 is a perspective view of an alternative form of preform that may be used for the porous metal portion of the tibial tray;

FIG. 33A is a table comparing different surface profile parameters for two groups of green machined titanium foam metal samples;

FIG. 33B is a table comparing different surface roughness parameters for one of the groups of the titanium foam metal samples of FIG. 33A;

FIG. 34A is a table comparing different surface profile parameters for two groups of salt blasted titanium foam metal samples;

FIG. 34B is a table comparing different surface roughness parameters for one of the groups of the titanium foam metal samples of FIG. 34A;

FIG. 35A is a table comparing different surface profile parameters for two groups of milled titanium foam metal samples;

FIG. 35B is a table comparing different surface roughness parameters for one of the groups of the titanium foam metal samples of FIG. 35A;

FIG. 36A is a table comparing different surface profile parameters for a group of ground titanium foam metal samples;

FIG. 36B is a table comparing different surface roughness parameters for the titanium foam metal samples of FIG. 36A;

FIG. 37A is a table comparing different surface profile parameters for two groups of titanium foam metal samples that had been turned on one type of lathe;

FIG. 37B is a table comparing different surface roughness parameters for both groups of the titanium foam metal samples of FIG. 37A;

FIG. 38A is a table comparing different surface profile parameters for a group of titanium foam metal samples that had been turned on another type of lathe;

FIG. 38B is a table comparing different surface roughness parameters for the titanium foam metal samples of FIG. 37A;

FIG. 39 is a table comparing different surface profile parameters for a group of polished titanium foam metal samples;

DETAILED DESCRIPTION OF THE DRAWINGS

Figure 1:
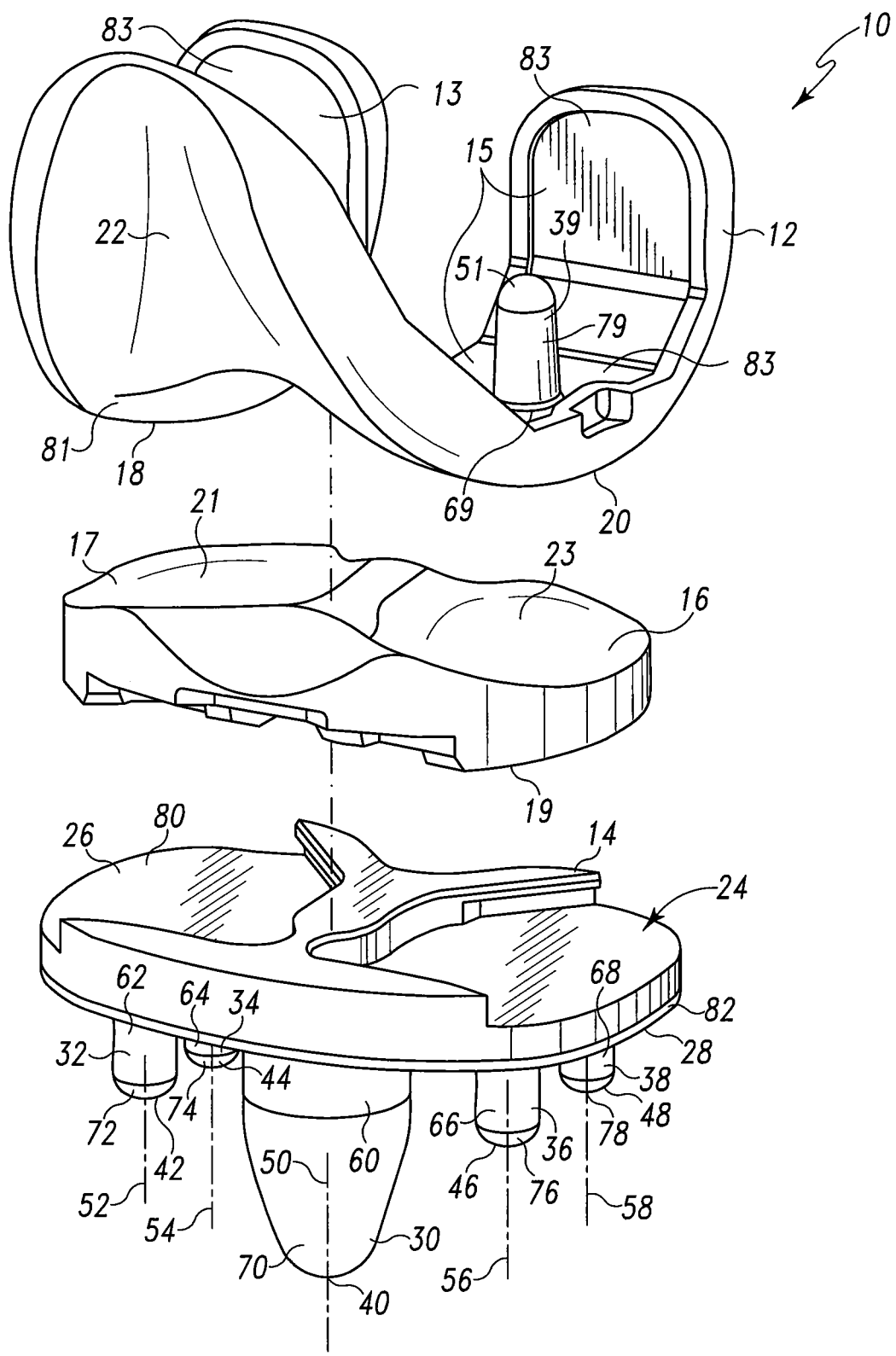
FIG. 1 is an exploded perspective view of a fixed-bearing knee prosthesis.
Figure 2:
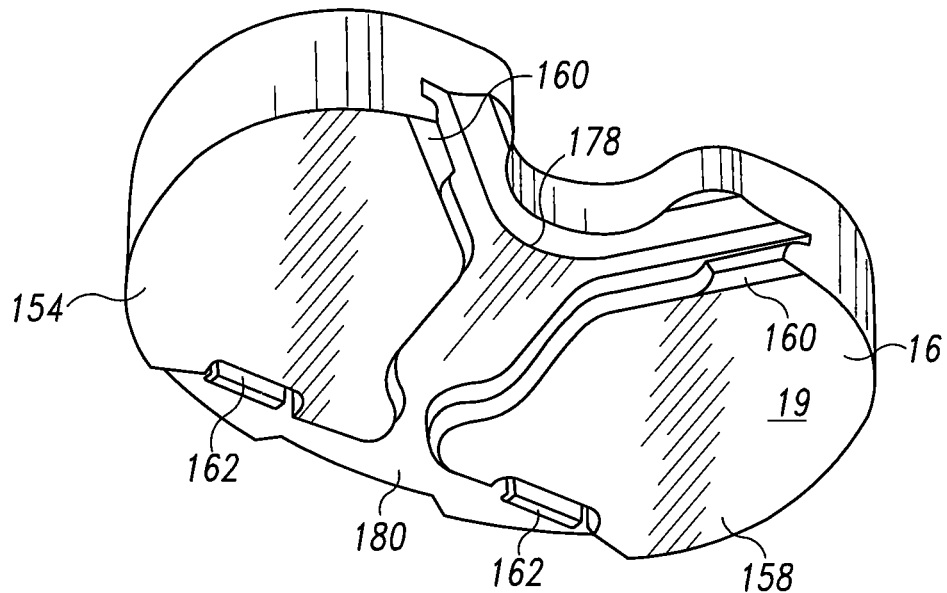
FIG. 2 is a bottom perspective view of the bearing of the knee prosthesis of FIG. 1.
Figure 3:
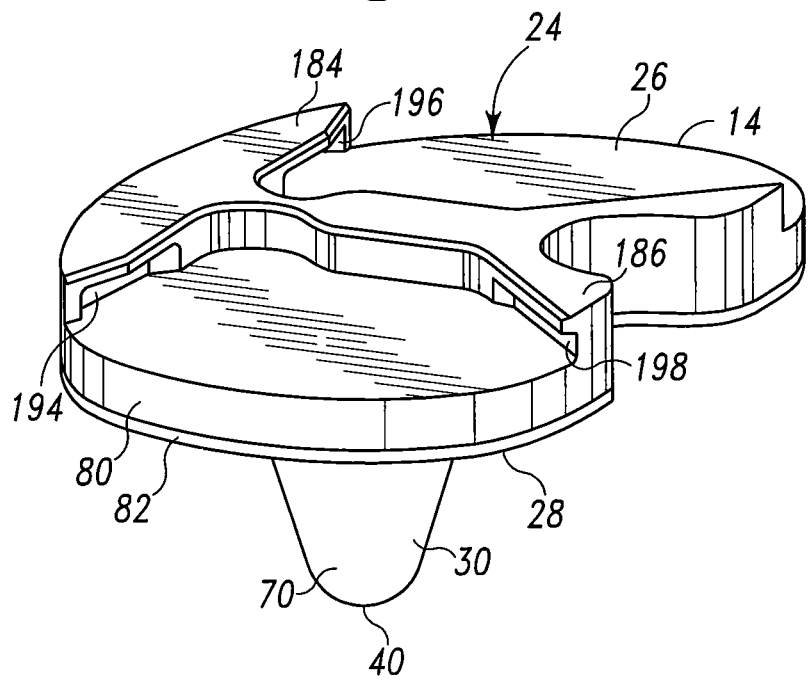
FIG. 3 is a perspective view of the tibial tray of the knee prosthesis of FIG. 1.

The following U.S. patent applications are related to the present application: "Prosthesis with Modular Extensions," filed by Anthony D. Zannis and Daren L. Deffenbaugh (DEP6035USCIP1, now U.S. Pat. No. 8,632,600); "Prosthesis For Cemented Fixation And Method Of Making The Prosthesis," filed by Daren L. Deffenbaugh and Anthony D. Zannis (DEP6035USCIP2, now U.S. Pat. No. 8,715,359); "Prosthesis With Cut-Off Pegs And Surgical Method," filed by Daren L. Deffenbaugh and Anthony D. Zannis (DEP6035USCIP3, published as U.S. Pub. No. 20110035017); and "Prosthesis With Composite Component," filed by Daren L. Deffenbaugh and Thomas E. Wogoman (DEP6035USCIP4, published as U.S. Pub. No. 20110035018). All of these patent applications are incorporated by reference herein in their entireties.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, there is shown a knee prosthesis 10. The knee prosthesis 10 includes a femoral component 12, a tibial tray 14, and a bearing 16. The illustrated knee prosthesis 10 is a fixed bearing knee prosthesis, meaning that no movement is intended to occur between the tibial tray 14 and the bearing 16. It should be understood that the principles of the present invention may also be applied to mobile bearing designs, such as rotating platform tibial trays, as well as to other joint prostheses.

The illustrated femoral component 12 includes two condylar articulation surfaces: a medial condyle articulation surface 18 and a lateral condyle articulation surface 20. These articulation surfaces 18, 20 are solid metal. The femoral component 12 is configured to be implanted into a surgically prepared end of the patient's femur (not shown), and is configured to emulate the configuration of the patient's natural femoral condyles. As such, the lateral condyle surface 20 and the medial condyle surface 18 are configured (e.g., curved) in a manner which mimics the condyles of the natural femur. The lateral condyle surface 20 and the medial condyle surface 18 are spaced apart from one another thereby defining an intercondylar articulation surface 22 therebetween. The intercondylar articulation surface 22 defines a patella groove shaped to receive and bear against a patella implant component (not shown). The intercondylar articulation surface 22 may comprise solid metal.

The femoral component 12 also includes bone-engaging surfaces 13, 15 opposite the articulation surfaces 18, 20, 22. Some or all of the bone-engaging surfaces 13, 15 may comprise porous metal (as described below) conducive to bony ingrowth. Alternatively, the bone-engaging surfaces of the femoral component may include cement pockets to facilitate cementing the component to the bone.

The femoral component 12 of FIG. 1 is a cruciate retaining component, although it should be understood that the principles of the present invention are applicable to cruciate substituting prosthetic knee systems as well.

The femoral component 12 may include features of standard, commercially available implants, such as those available from DePuy Orthopaedics, Inc., Warsaw, Ind., as well as those available from other suppliers of prosthetic knee systems. The femoral component 12 may also include features described in the following United States patent applications, the disclosures of which are incorporated by reference herein in their entireties: "Orthopaedic Knee Prosthesis Having Controlled Condylar Curvature," U.S. Pub. No. 20100036500A1, U.S. patent application Ser. No. 12/488,107; "Posterior Cruciate-Retaining Orthopaedic Knee Prosthesis Having Controlled Condylar Curvature," U.S. Pub. No. 2009032664A1, U.S. patent application Ser. No. 12/165,574; "Orthopaedic Femoral Component Having Controlled Condylar Curvature," U.S. Pub. No.

20090326667A1, U.S. patent application Ser. No. 12/165, 579; "Posterior Stabilized Knee Prosthesis," U.S. Pub. No. 20090326666A1, U.S. patent application Ser. No. 12/165, 582; and "Posterior Stabilized Orthopaedic Knee Prosthesis Having Controlled Condylar Curvature," U.S. Pub. No. 20090326665A1, U.S. patent application Ser. No. 12/165, 575.

The articulation surfaces of the femoral component 12 may be constructed from a biocompatible metal, such as stainless steel, titanium, cobalt chrome alloy or titanium alloy, although other materials may also be used. Commonly used alloys include titanium alloy Ti-6Al-4. In one aspect of the present invention, the articulation surfaces 18, 20, 22 of the femoral component 12 comprise a titanium alloy (such as Ti-6Al—, for example) and the bone-engaging surfaces 13, 15 comprise titanium metal foam (such as a foam made of commercially pure titanium powder, 325 mesh (<45 um), produced by a hydride-dehydride process and that meets the ASTM F-1580 standard, available from Phelly Materials, Inc., Bergenfield, N.J., Part No. THD325 for example) or a mix of such a powder with a compatible titanium alloy powder, such as Ti-6Al-4V. As discussed in more detail below, the titanium metal foam may comprise a titanium foam preform bonded to the solid titanium alloy through sintering.

As shown in FIG. 1, the bearing component 16 has a proximal articulation surface 17 and a distal mounting surface 19 opposite the proximal articulation surface 17. The proximal articulation surface 17 of the bearing 16 includes a medial bearing surface 21 configured to articulate with the medial condyle 18 of the femoral component 12 and a lateral bearing surface 23 configured to articulate with the lateral condyle 20 of the femoral component 12. The bearing component 16 is modular, and is assembled with the tibial tray 14 intraoperatively and secured thereto through a mechanical interlocking mechanism, as described in more detail below.

The bearing 16 may be made of a polymeric material. Suitable polymeric materials for the bearing 16 include ultrahigh molecular weight polyethylene (UHMWPE). The UHMWPE may comprise a cross-linked material, for example. Techniques for crosslinking, quenching, or otherwise preparing UHMWPE are described in numerous issued U.S. patents, examples of which include: U.S. Pat. No. 5,728,748 (and its counterparts) issued to Sun, et al.; U.S. Pat. No. 5,879,400 issued to Merrill et al.; U.S. Pat. No. 6,017,975 issued to Saum, et al.; U.S. Pat. No. 6,242,507 issued to Saum et al.; U.S. Pat. No. 6,316,158 issued to Saum et al.; U.S. Pat. No. 6,228,900 issued to Shen et al.; U.S. Pat. No. 6,245,276 issued to McNulty et al.; and U.S. Pat. No. 6,281,264 issued to Salovey et al. The disclosure of each of these U.S. patents is incorporated by reference herein in their entireties. The UHMWPE of the bearing material may be treated to stabilize any free radicals present therein, such as through the addition of an antioxidant such as vitamin E. Techniques for stabilizing UHMWPE with antioxidants are disclosed, for example, in U.S. Pat. Pub. No. 20070293647A1 (U.S. patent application Ser. No. 11/805,867) and U.S. Pat. Pub. No. 20030212161A1 (U.S. patent application Ser. No. 10/258,762), both entitled "Oxidation-Resistant And Wear-Resistant Polyethylenes For Human Joint Replacements And Methods For Making Them," the disclosures of which are incorporated herein in their entireties. It should be understood that the present invention is not limited to any particular UHMWPE material or to UHMWPE material for the bearing 16 unless expressly called for in the claims. It is expected that other materials for the bearing 16 are or will become available that will be useful in applying the principles of the present invention.

The tibial tray 14 includes a platform 24 having a solid metal proximal mounting surface 26 and an opposite distal bone-engaging surface 28. The illustrated tibial tray 14 also includes a plurality of extensions 30, 32, 34, 36, 38 extending distally from the distal bone-engaging surface 28 of the platform to distal ends 40, 42, 44, 46, 48 along longitudinal axes 50, 52, 54, 56, 58 intersecting the distal surface 28 of the platform 24. Each extension 30, 32, 34, 36, 38 has an axial length, shown, for example, as $L_1$ and $L_2$ in FIG. 5 and a thickness, shown, for example, as $T_1$ and $T_2$ in FIG. 5.

The femoral component 12 may also include extensions. For example, pegs may extend proximally from the bone-engaging surfaces 13, 15 of the femoral component 12. One such peg is illustrated in FIG. 1 at 39. This peg also has a thickness and a length.

In the illustrated femoral component and tibial tray, each extension 30, 32, 34, 36, 38, 39 extends outward from a junction with the bone-engaging surfaces 13, 15, 28 of their respective implant components 12, 14 to their opposite ends 40, 42, 44, 46, 48, 51. Examples of such junctions are shown in FIG. 1 at 69, in FIG. 5 at 60, 62 and 66 and in FIG. 7 at 60A, 62A, 66A. The extensions 30, 32, 34, 36, 38, 39 have exposed outer surfaces past the junctions; examples of such exposed outer surfaces are shown at 79 in FIG. 1, at 70, 72 and 76 in FIG. 5 and at 70A, 72A and 76A in FIG. 7.

The extensions 30, 32, 34, 36, 38 of the first and second illustrated tibial tray embodiments define a stem 30, 30A and four spaced pegs 32, 34, 36, 38, 32A, 34A, 36A, 38A. The stem 30, 30A and pegs 32, 34, 36, 38, 32A, 34A, 36A, 38A are configured to be implanted into a surgically prepared end of a patient's tibia (not shown) and are configured for stabilizing the tibial component 14, 14A when implanted in a bone of a patient. The stem 30, 30A is generally in the central sagittal plane of the tibial component, and the pegs 32, 34, 36, 38, 32A, 34A, 36A, 38A are spaced from the central sagittal plane of the tibial component.

Figure 4:
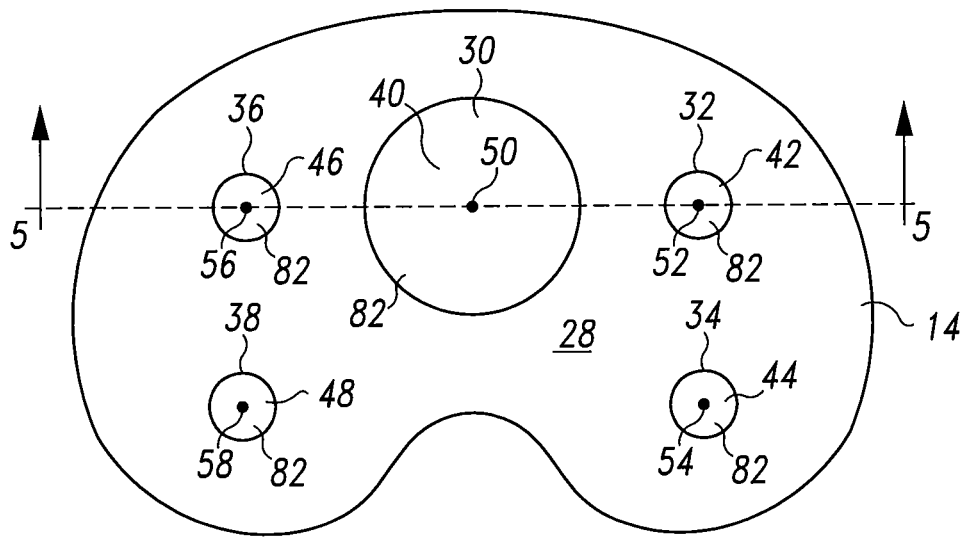
FIG. 4 is a bottom plan view of the tibial tray of FIG. 1.
Figure 5:
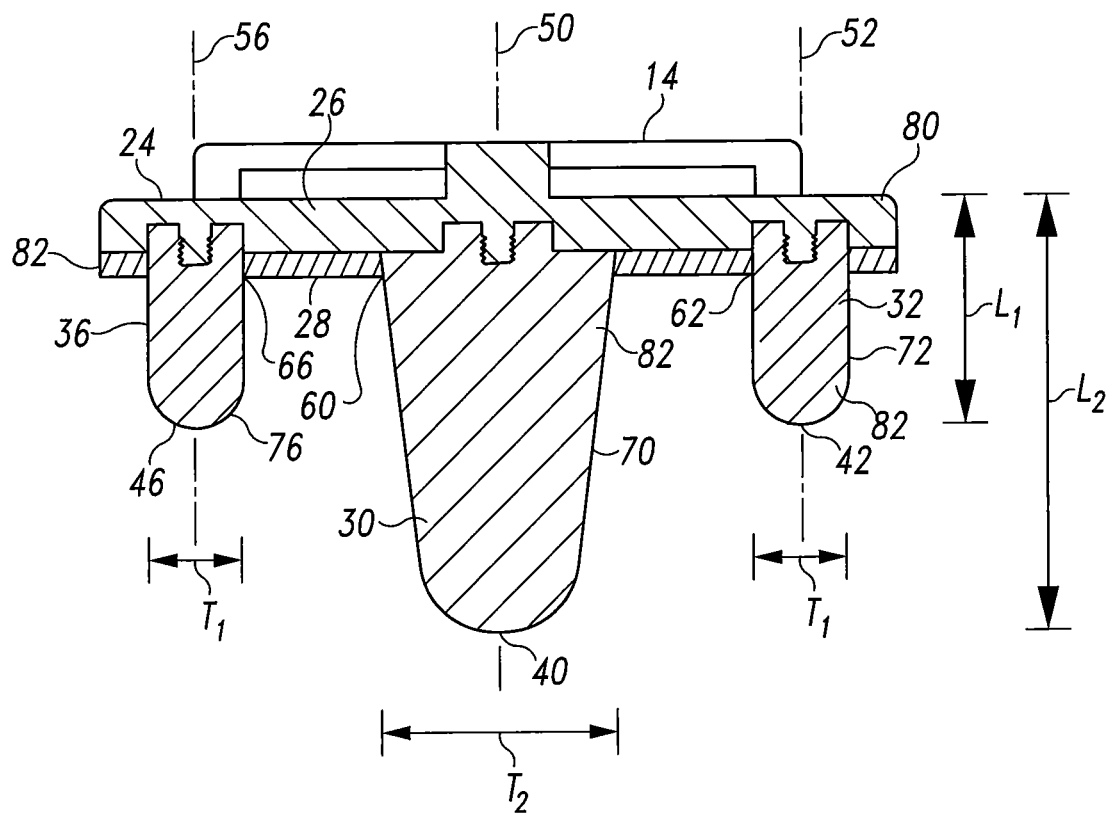
FIG. 5 is a cross sectional view of the tibial tray of FIG. 4 taken along the line 5-5 of FIG. 4, as viewed in the direction of the arrows.

The stem 30, 30A may be shaped as a standard stem for tibial trays, tapering from the junction 60, 60A with the bone-engaging surface 28, 28A of the tibial tray 14, 14A to its distal end 40, 40A. Each of the tibial pegs 32, 34, 36, 38 in the embodiment of FIGS. 1, 4 and 5 is circular in transverse cross-section and end view. Other shapes may also be used for the pegs. The pegs may be tapered or cylindrical. The pegs may be a combination of shapes, such as a combination of cylindrical and hexagonal, as shown in FIG. 12 at 32B. Alternatively, the pegs may be hexagonal in cross-section and end view, as shown in FIG. 13 at 32C. In FIGS. 12 and 13, the reference numbers are the same as those used in the description of the embodiment of FIGS. 1, 4 and 5 for similar parts, followed by the letters "B" and "C".

The distal end surfaces of the stem and pegs could be flat, spheroidal or some other shape. In the embodiment of FIGS. 1, 4 and 5, the free ends 40, 42, 44, 46, 48, 51 are generally spheroidal. In the embodiments of FIGS. 12 and 13, the distal ends 42B, 42C are flat. It should be understood that the invention is not limited to any particular shape of peg or stem unless expressly set forth in the claims.

Figure 6:
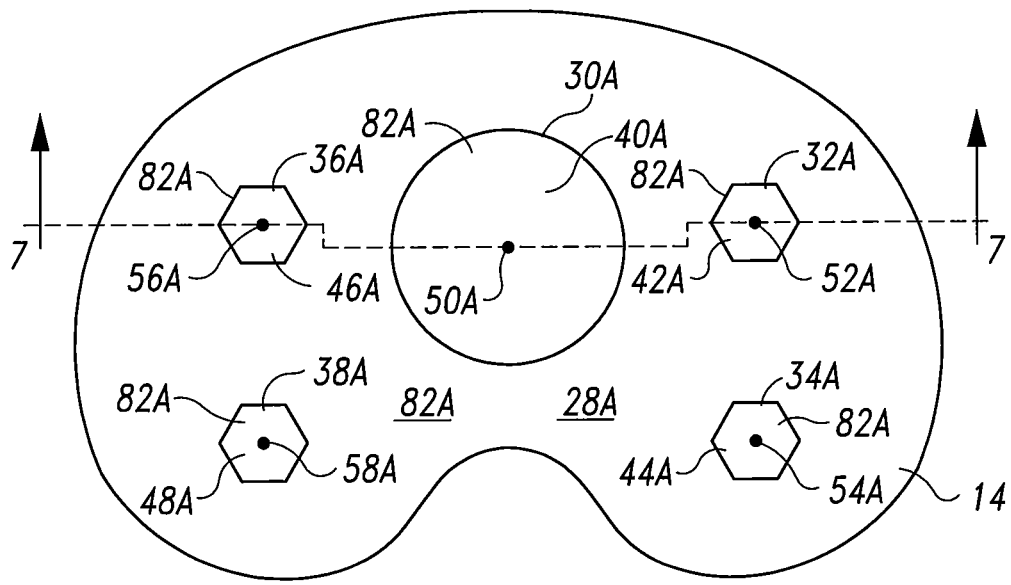
FIG. 6 is a bottom plan view of an alternative embodiment of a tibial tray that may be used in the present invention.
Figure 7:
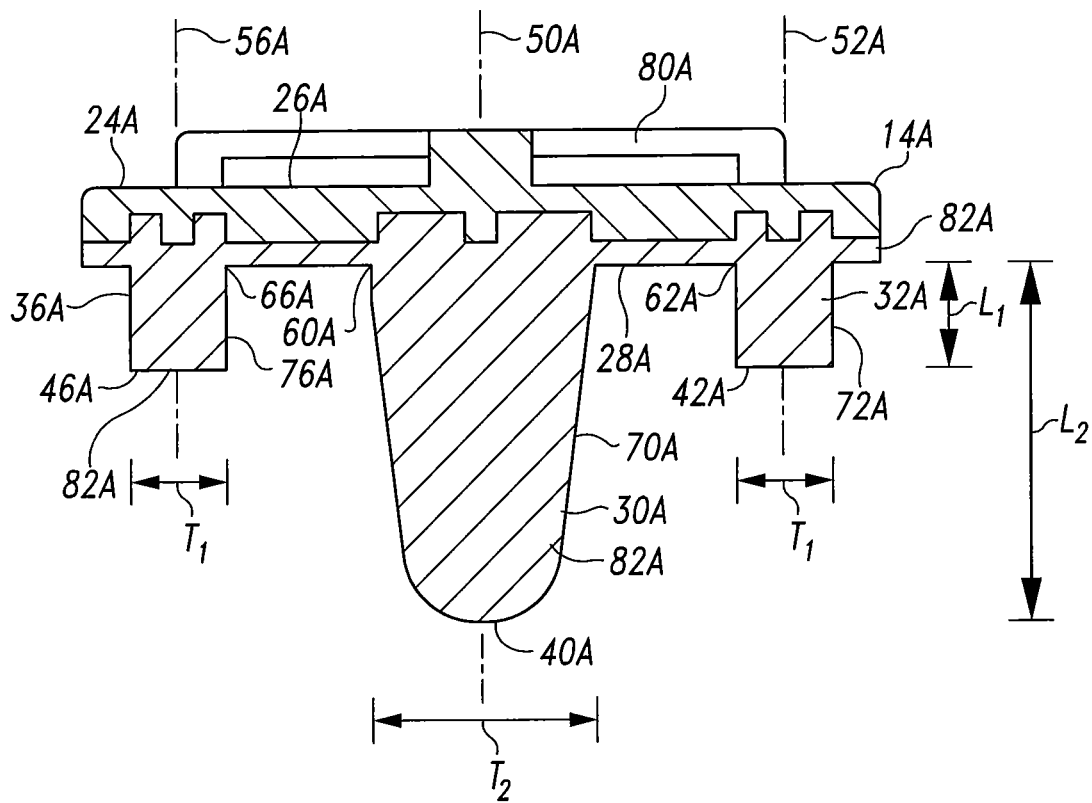
FIG. 7 is a cross sectional view of the tibial tray of FIG. 6 taken along the line 7-7 of FIG. 6, as viewed in the direction of the arrows.

Another alternative embodiment is illustrated in FIGS. 6-7, where the same reference numbers have been used as those used in describing corresponding or similar parts in the embodiment of FIGS. 1 and 4-5, followed by the letter "A". As described in more detail below, in the embodiment of FIGS. 6-7, all of the extensions 30A, 32A, 34A, 36A, 38A are part of a single integral preform. The embodiments may share features as described above and below. Differences between the embodiments are described above and below.

The tibial trays 14, 14A illustrated in FIGS. 1 and 3-7 are composites of two materials; each tray 14, 14A includes solid metal portions 80, 80A and porous metal portions 82, 82A. The solid metal portions 80, 80A of the illustrated tibial trays 14, 14A define the proximal mounting surfaces 26, 26A of the platforms 24, 24A and bear against the distal mounting surface 19 of the bearing component 16 when assembled. The femoral component of FIG. 1 may also be a composite of a solid metal portion 81 and a porous metal portion 83, with the solid metal portion 81 defining the articulating surfaces 18, 20, 22.

The porous metal portions 82, 82A, 83 of the tibial tray 14, 14A and femoral component 12 define the distal bone-engaging surfaces 28, 28A of the tibial platform 24, 24A and the bone-engaging surfaces 13, 15 of the femoral component 12. These porous metal bone-engaging surfaces 13, 15, 28, 28A face the bone of the resected proximal surface of the tibial plateau and resected surfaces of the distal femur when implanted, and define a material that is conducive to bone ingrowth to allow for uncemented fixation of the tibial platform 24, 24A to the proximal tibia and the femoral component 12 to the distal femur. As described in more detail below, the porous metal portion 82, 82A of the tibial tray 14, 14A extends proximally from the distal bone-engaging surface 28, 28A and is sintered to the solid metal portion 80, 80A at a location between the distal bone-engaging surface 28, 28A and the proximal mounting surface 26, 26A of the platform 24, 24A. The femoral component 12 is similarly constructed, with the porous metal portion 83 sintered to the solid metal portion 81 at a location between the bone-engaging surfaces 13, 15 and the articulating surfaces 18, 20, 22.

Figure 8:
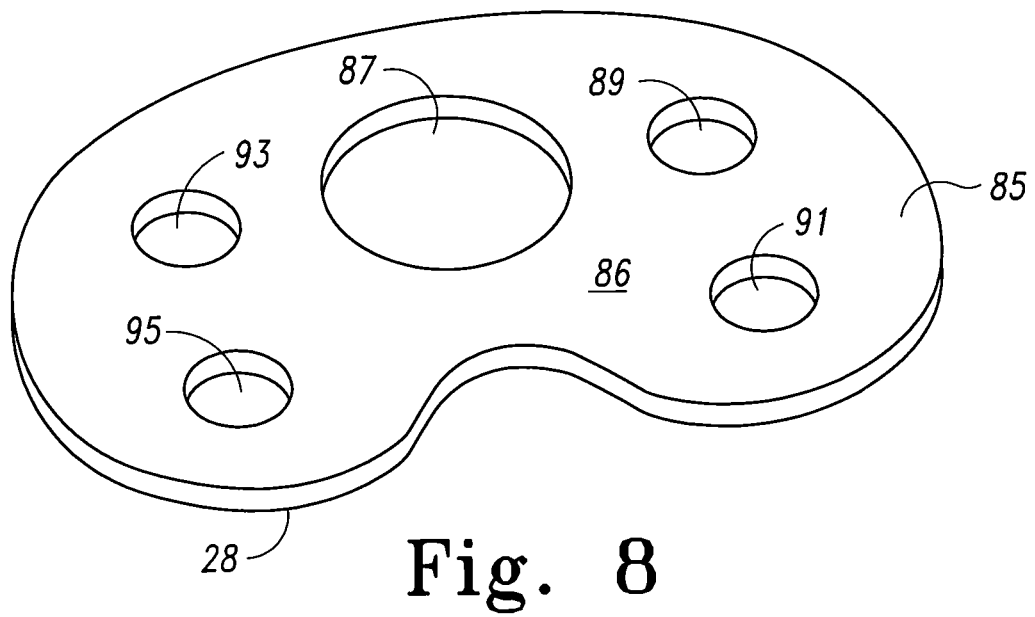
FIG. 8 is a perspective view of a preform for the tibial tray platform portion of the porous metal portion of the tibial tray of FIGS. 1-5.
Figure 9:
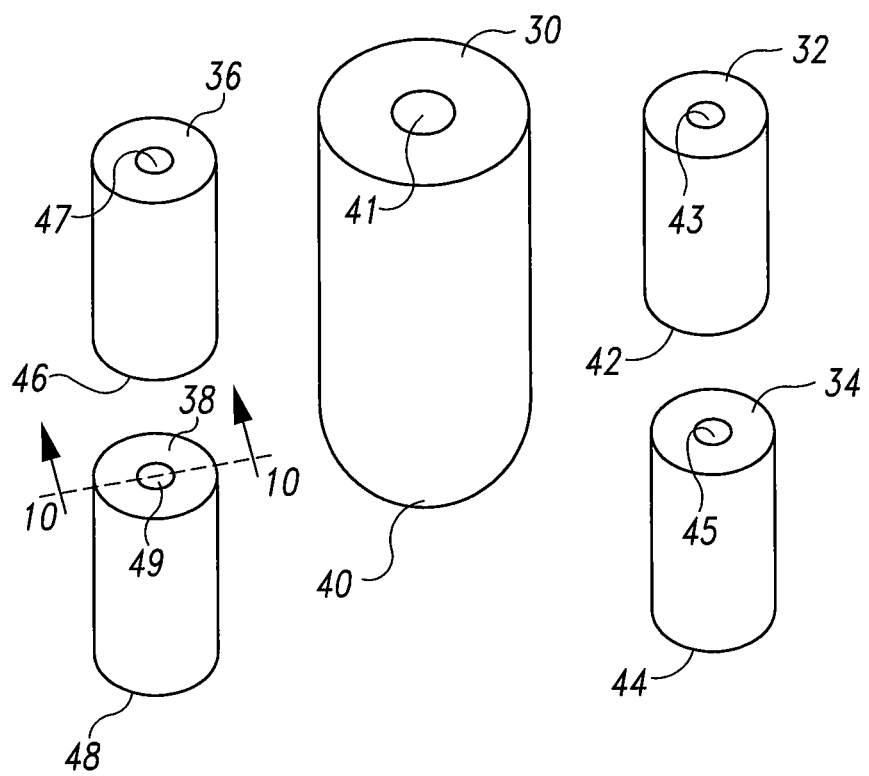
FIG. 9 is a perspective view of a set of preforms for the extensions of the porous metal portion of the tibial tray of FIGS. 1-5.

The porous metal portions 82, 82A, 83 of the tibial tray 14 and femoral component 12 may comprise preforms or a plurality of preforms. A first example of a set of porous metal preforms for a tibial tray 14 is illustrated in FIGS. 8-9. This set of porous metal preforms includes a base preform 85 with an upper surface 86 opposite from the distal bone-engaging surface 28. The upper surface 86 becomes the interface with the solid metal portion 80 of the tibial tray 14 when the porous metal base preform 85 is sintered to the solid metal portion 80 to make the tibial tray 14. As described in more detail below, the first illustrated base preform 85 includes a plurality of smooth cylindrical bores or openings 87, 89, 91, 93, 95 extending from the upper surface 86 to the distal bone-engaging surface 28.

Figure 10:
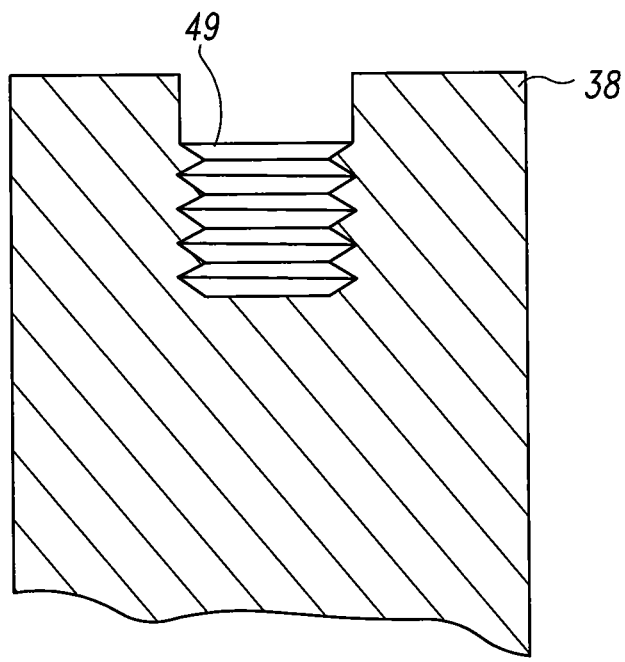
FIG. 10 is a cross sectional view of the proximal end of the peg preform of FIG. 9 taken along line 10-10 of FIG. 9, as viewed in the direction of the arrows.

As illustrated in FIG. 9, the extensions 30, 32, 34, 36, 38 in the first set of porous metal preforms are discrete components, separate from the base preform 85 before being sintered together. The illustrated extension preforms are circular in transverse cross-section, with diameters substantially the same as the diameters of the bores 87, 89, 91, 93, 95 in the base preform 85. Portions of the extensions adjacent to the proximal ends of the extensions fit through the bores 87, 89, 91, 93, 95 and make contact with the walls of the base preform so that the preform 85 and extensions 87, 89, 91, 93, 95 may be sintered together. The proximal ends of the discrete extensions include blind bores 41, 43, 45, 47, 49 aligned along the longitudinal axes 50, 52, 54, 56, 58 of the extensions 30, 32, 34, 36, 38. The bores 41, 43, 45, 47, 49 are threaded in this embodiment. For clarity of illustration, FIG. 9 does not show the threads in these bores 41, 43, 45, 47, 49. An example of such a threaded bore 49 is shown in longitudinal cross-section in FIG. 10.

Other shapes of extensions may be used in combination with the base preform 85. For example, the extensions corresponding to the pegs may comprise a combination of a cylindrical portion and a portion that is hexagonal in transverse cross-section. Such a peg is shown in FIG. 12 at 32B; the cylindrical portion is shown at 100 and the hexagonal portion is shown at 102. This peg preform also has a flat end surface 42B opposite the end surface 106 that includes the threaded bore 43B.

Another example of an extension that may be used in the present invention is shown in FIG. 13 at 32C. In this example, the extension 32C is hexagonal in transverse cross-section and in end view. The extension includes two flat ends 42C, 106C with a blind bore 43C in one end 106C. In this example, the blind bore 43C is not threaded. Instead, the walls of the bore 43C define a Morse taper bore for receipt of a Morse taper post as described in more detail below. The walls defining the bore 43C may be tapered at an angle of, for example 3-5°. The bore is widest at the end 106C and most narrow between the end 106C and the end 42C. Peg preforms such as those illustrated in FIG. 13 could be used with a tibial platform preform similar to that illustrated in FIG. 8, except the bores or holes 89, 91, 93, 95 would have hexagonal shapes to receive and hold the extension 32C.

Figure 15:
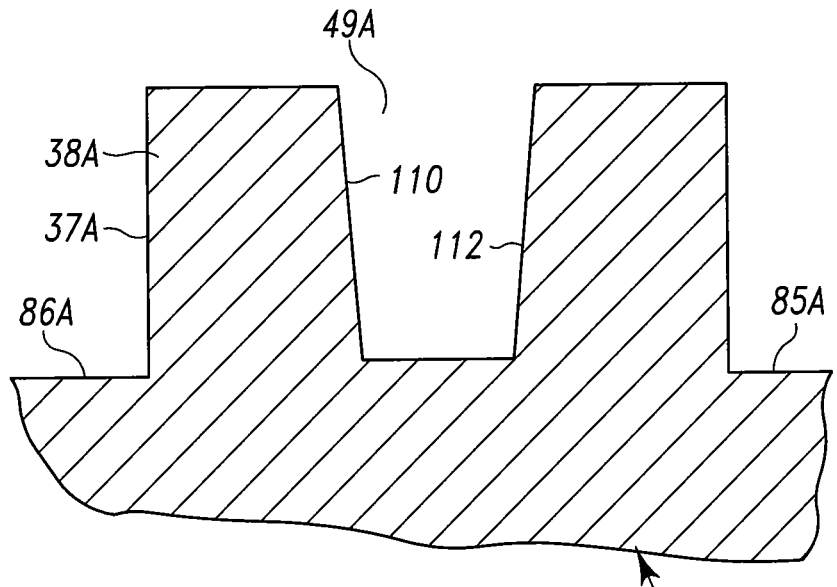
FIG. 15 is a cross sectional view of the proximal end of a portion of the preform of FIG. 14, taken along line 15-15 of FIG. 14, as viewed in the direction of the arrows.

An example of a porous metal preform utilizing extensions shaped like those of FIG. 13 is shown in FIG. 14. In this example, the porous metal preform 84A includes a base portion 85A and integral extensions 30A, 32A, 34A, 36A, 38A. The extensions 32A, 34A, 36A, 38A correspond with pegs and the extension 30A corresponds with the stem of the tibial tray. In this embodiment, the extension 30A corresponding with the stem is circular in transverse cross-section, although it should be understood that other shapes may be used. On the proximal side of the base 85A, an annular raised portion 29A, 31A, 33A, 35A, 37A of each extension extends above the planar proximal surface 86A of the base 85A. Each extension includes a longitudinal bore or opening 41A, 43A, 45A, 47A, 49A. As discussed above with respect to FIG. 13, in this embodiment, the longitudinal bores or openings 41A, 43A, 45A, 47A, 49A are Morse taper bores tapering in a distal direction. An enlarged cross-sectional view of one of the annular raised portions 37A and its associated bore 49A is shown in FIG. 15 as an illustrative example; the walls 110, 112 defining the tapered bore 49A may be angled at any suitable angle for a Morse taper bore, such as, for example, 3-5°. The annular projections 29A, 31A, 33A, 35A, 37A may be cylindrical in shape, like that shown at 29A, or may have some other shape, such as the hexagonal shape (in transverse cross-section and plan view) like those shown at 31A, 33A, 35A and 37A.

Figure 16:
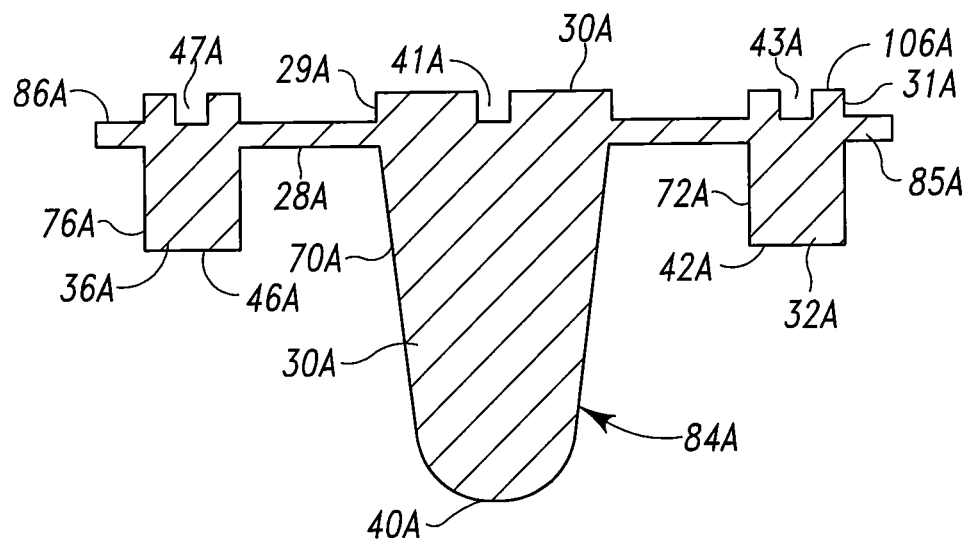
FIG. 16 is a cross sectional view of the porous metal preform of FIG. 14, taken along line 16-16 of FIG. 14, as viewed in the direction of the arrows.

A cross-section of the porous metal preform 84A is shown in FIG. 16 as an example. The porous metal preform 84A can be made as a single, integral piece in the molding process and can be otherwise processed in standard ways, such as by machining to create particular features. FIG. 7 illustrates the preform 84A of FIGS. 14-16 in combination with a solid metal portion 80A to form the tibial tray 14A.

Figure 17:
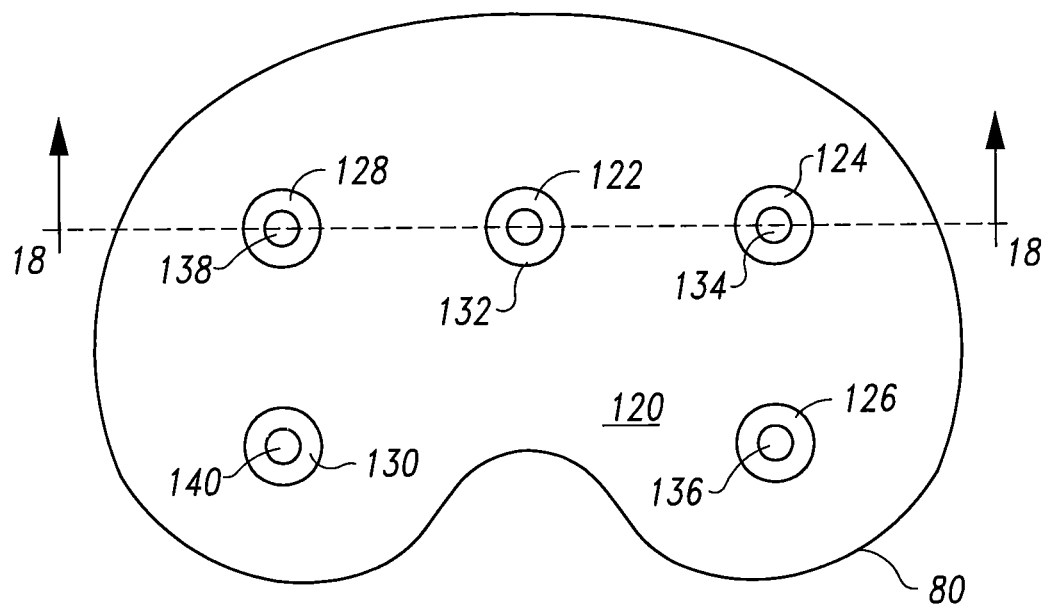
FIG. 17 is a bottom plan view of the solid metal preform for the tibial tray of FIGS. 4-5, for use with the porous metal preforms of FIGS. 8-9.
Figure 19:
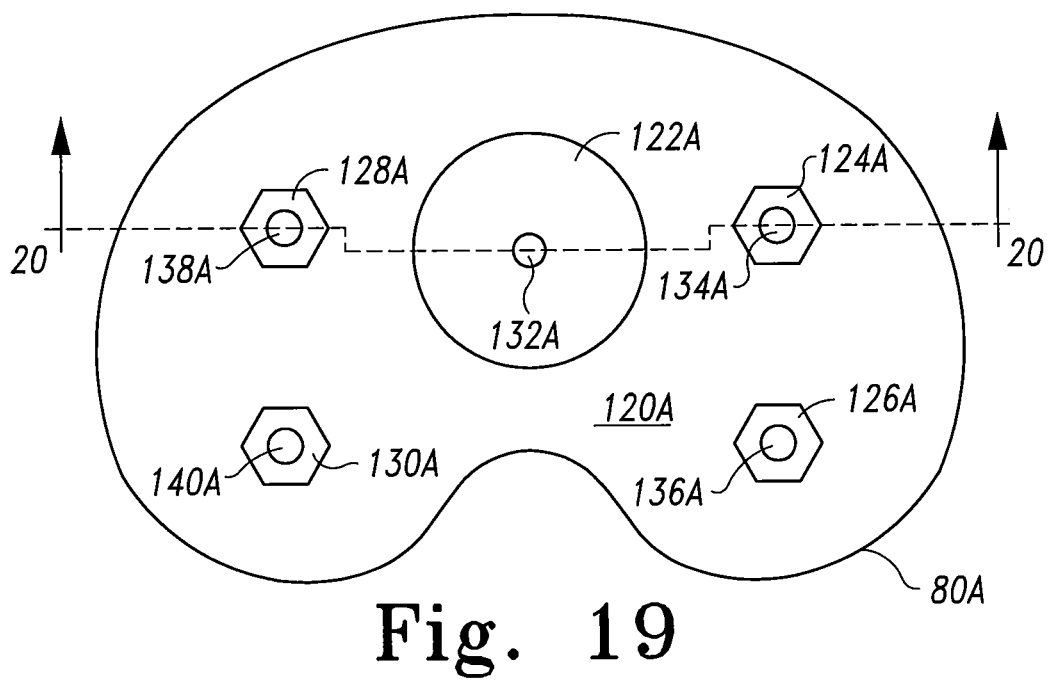
FIG. 19 is a bottom plan view of an alternative solid metal preform, for use with the porous metal preform of FIGS. 14 and 16.

Referring back to the solid metal portion 80 of the tibial tray 14, a first example of a distal surface 120 of the solid metal portion is illustrated in FIG. 17. The distal surface 120 is opposite the proximal mounting surface 26 of the platform 24 of the tibial tray 14 of FIG. 1. As there shown, the distal surface 120 includes a plurality of recesses 122, 124, 126, 128, 130. A stud 132, 134, 136, 138, 140 is present within each recess 122, 124, 126, 128, 130. The distal surface of a second example of the solid metal portion 80A of a tibial tray is illustrated in FIG. 19. As there shown, the distal surface 120A also includes a plurality of recesses 122A, 124A, 126A, 128A, 130A. A stud 132A, 134A, 136A, 138A, 140A is present within each recess 122A, 124A, 126A, 128A, 130A.

Figure 18:
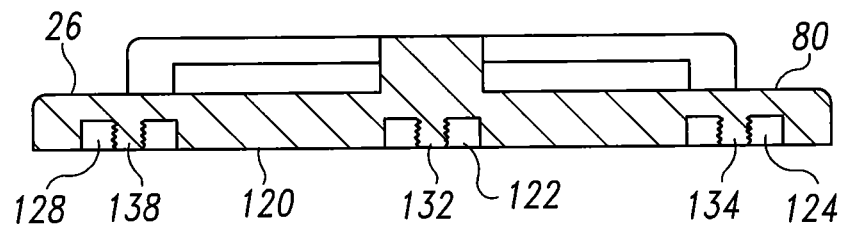
FIG. 18 is a cross sectional view of the solid metal preform of FIG. 17, taken along line 18-18 of FIG. 17, as viewed in the direction of the arrows.

The recesses 122, 124, 126, 128, 130 in the embodiment of FIGS. 17-18 are configured to receive the cylindrical ends of the extensions 30, 32, 34, 36, 38 and the studs 132, 134, 136, 138, 140 are threaded and complementary to the threaded bores 41, 43, 45, 47, 49 so that the extensions 30, 32, 34, 36, 38 may be threaded onto the studs 132, 134, 136, 138, 140 to mount the extensions to the studs 132, 134, 136, 138, 140. Preferably, the recesses 122, 124, 126, 128, 130 and extensions 30, 32, 34, 36, 38 are shaped so that there is metal-to-metal contact between the outer surfaces of the extensions 30, 32, 34, 36, 38 and the walls defining the recesses 122, 124, 126, 128, 130 so that the extensions 30, 32, 34, 36, 38 may be sintered to the solid metal portion 80.

Figure 20:
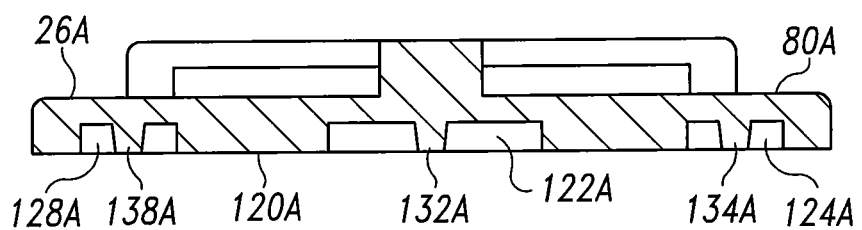
FIG. 20 is a cross sectional view of the solid metal preform of FIG. 19, taken along line 20-20 of FIG. 19, as viewed in the direction of the arrows.

The recesses 122A, 124A, 126A, 128A, 130A in the embodiment of FIGS. 19-20 are configured to receive the annular raised portions 29A, 31A, 33A, 35A, 37A of the preform 84A (or ends of the extensions 30A, 32A, 34A, 36A, 38A) and the studs 132A, 134A, 136A, 138A, 140A are tapered and complementary to tapered bores 41A, 43A, 45A, 47A, 49A so that the preform 84A may be frictionally mounted onto the studs 132A, 134A, 136A, 138A, 140A. The recesses 122A, 124A, 126A, 128A, 130A and annular raised portions 29A, 31A, 33A, 35A, 37A have complementary shapes (hexagonal in transverse cross-sections) so that there is metal-to-metal contact between the annular raised portions 29A, 31A, 33A, 35A, 37A and the walls defining the recesses 122A, 124A, 126A, 128A, 130A so that the preform 84A may be sintered to the solid metal portion 80A.

Figure 11:
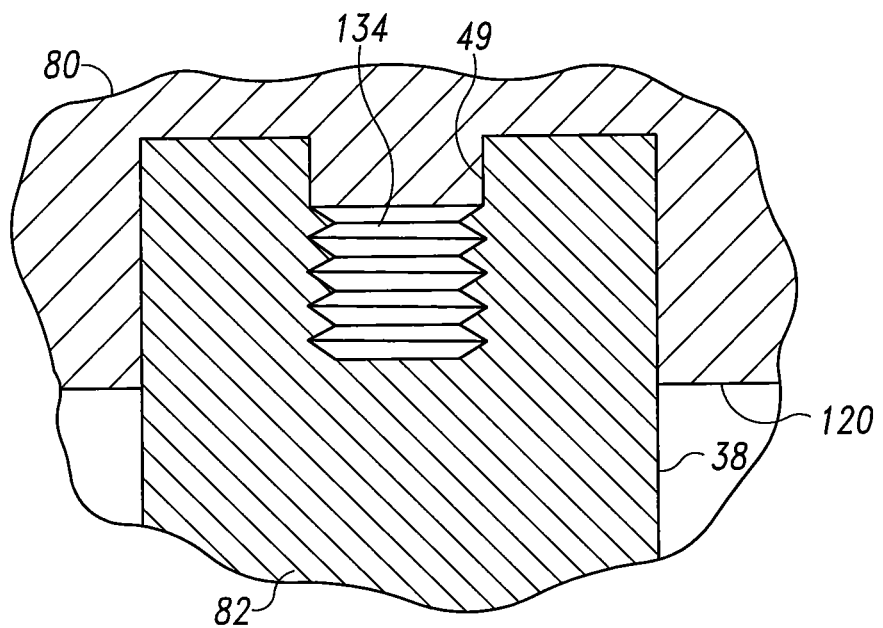
FIG. 11 is a cross sectional view similar to FIG. 10, showing the proximal end of the peg preform mounted on the solid metal portion of the tray.
Figure 21:
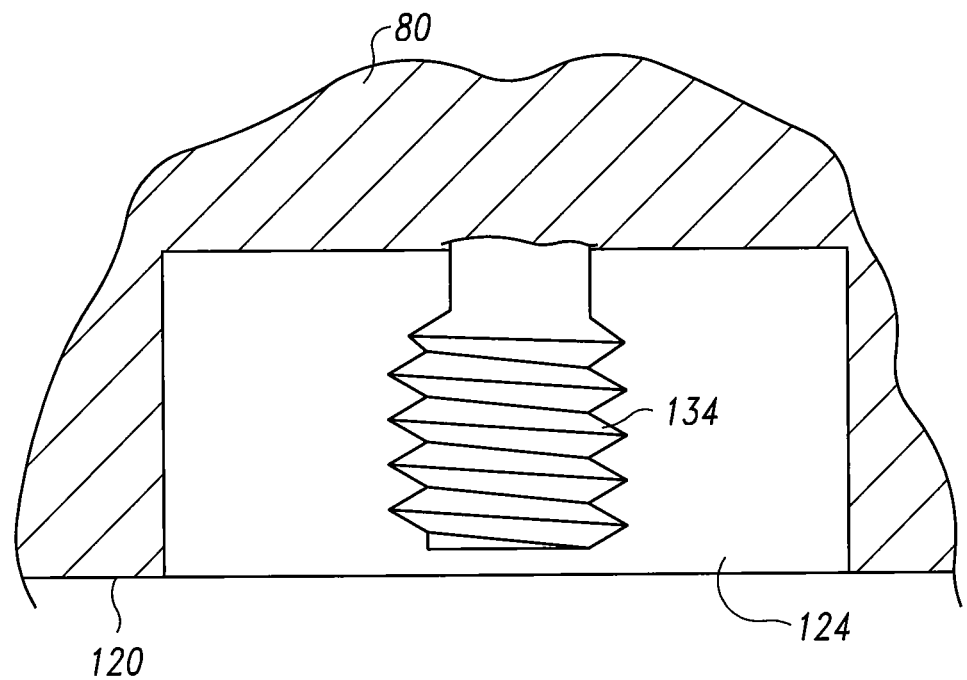
FIG. 21 is an enlarged partial cross sectional view of a portion of the solid metal preform of FIGS. 17-18
Figure 22:
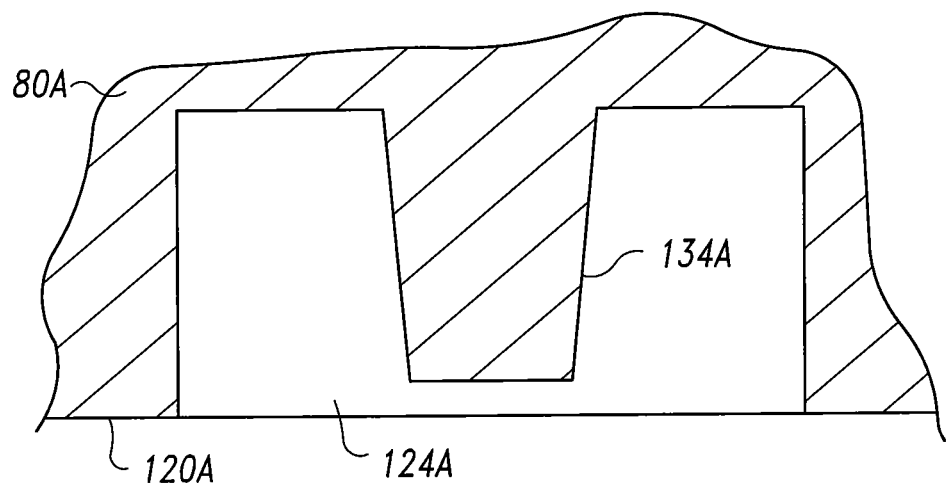
FIG. 22 is an enlarged cross sectional view of a portion of the solid metal preform of FIGS. 19-20.

Examples of configurations for studs are shown in FIGS. 21-22. The studs may be threaded, such as stud 134 shown in FIG. 21 to allow for a threaded connection between the studs and the corresponding threaded bores of the extensions; such a connection is illustrated in FIG. 11, where threaded stud 134 is shown connected with extension 38 through such a threaded connection.

Figure 23:
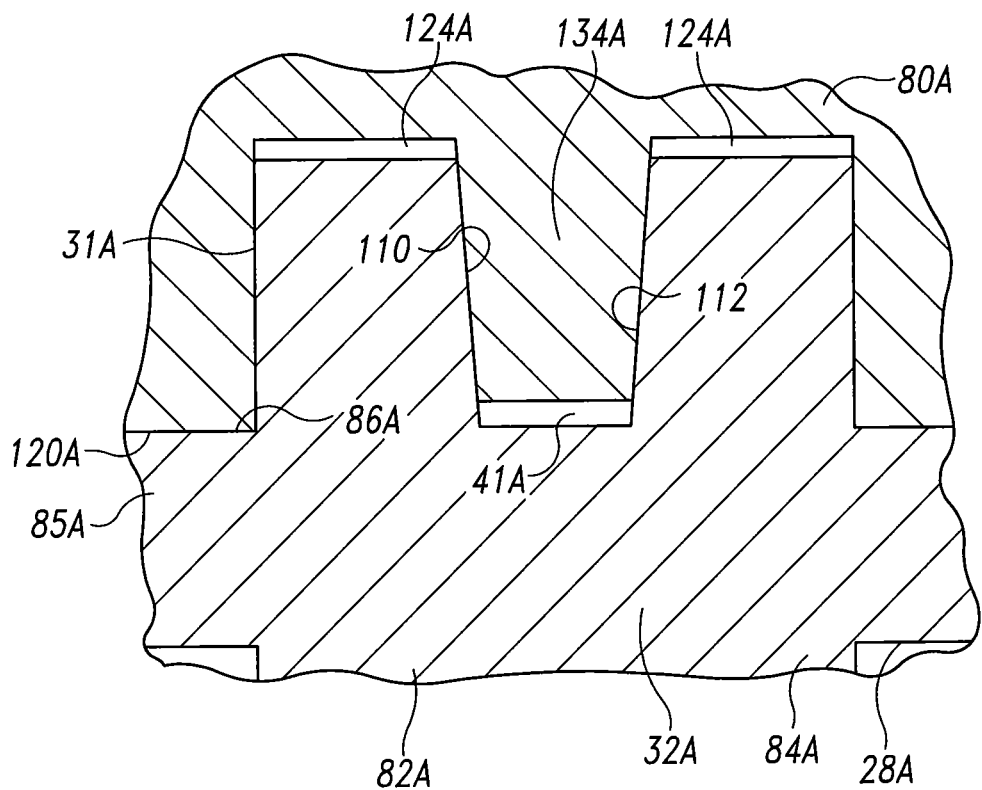
FIG. 23 is a view similar to FIG. 22, showing in cross section a portion of the solid metal preform of FIGS. 19-20 and 22 assembled with the porous metal preform of FIGS. 14 and 16.

The studs may alternatively comprise Morse taper posts having a Morse taper (generally about 3-5°); such a stud is shown in FIG. 22 at 134A. Generally, the studs are sized, shaped and positioned to be received within the Morse taper bore (generally about 3-5°) of a corresponding extension so that the extensions may be mounted on the studs. Such a connection is illustrated in FIG. 23, where Morse taper stud 134A is shown engaged with Morse taper bore 41A in preform 84A. It should be understood that the mounting mechanisms illustrated in FIGS. 21-22 are provided as examples only; other suitable structures may be used for mounting the extensions 30, 32, 34, 36, 38 and preform 84A to the corresponding solid metal portion 80, 80A, and the invention is not limited to any particular mounting structure unless expressly called for in the claims.

Figure 28:
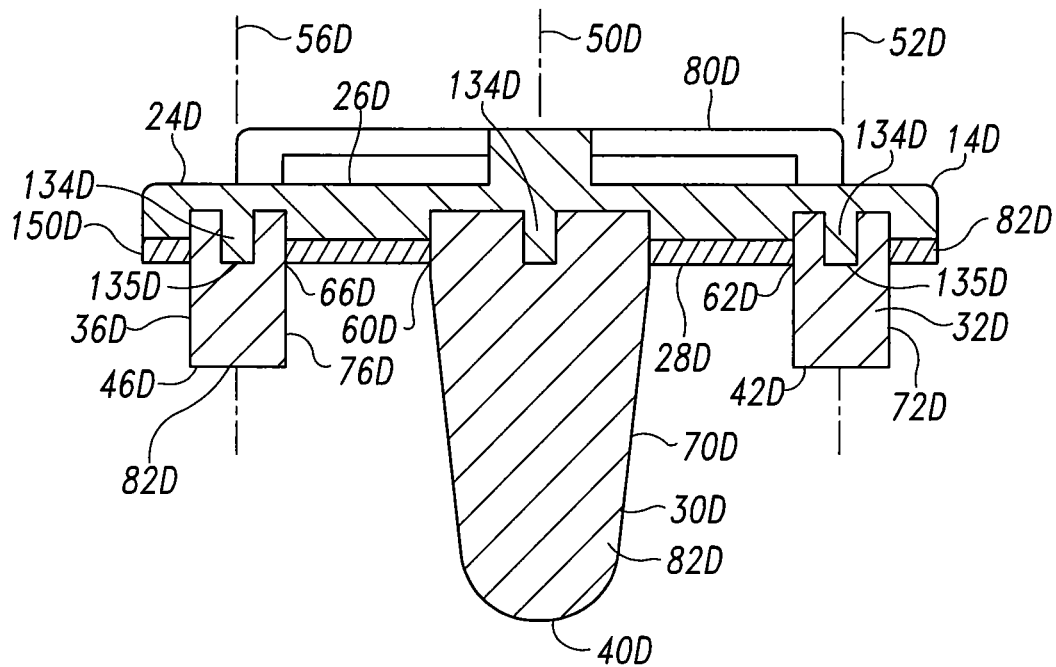
FIG. 28 is a cross-sectional view, similar to FIGS. 5 and 7, of an alternative embodiment of a tibial tray that may be used in the present invention.
Figure 29:
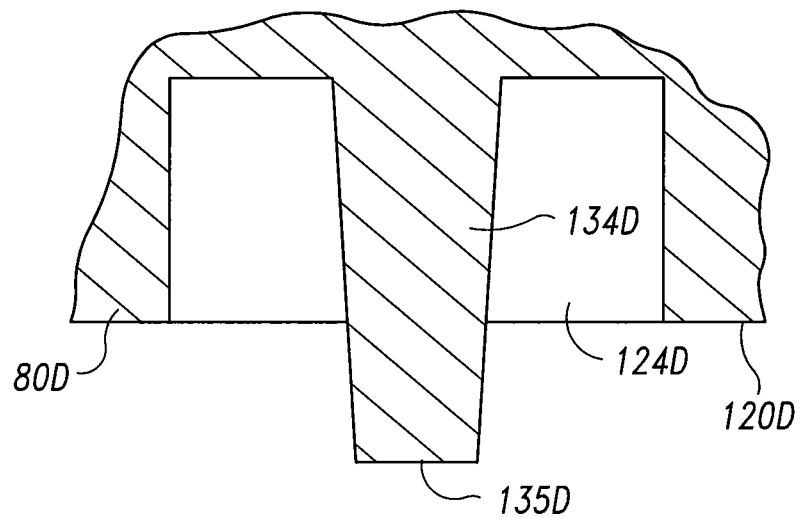
FIG. 29 is an enlarged cross-sectional view of one of the studs and recesses of the metal preform of FIG. 28.
Figure 30:
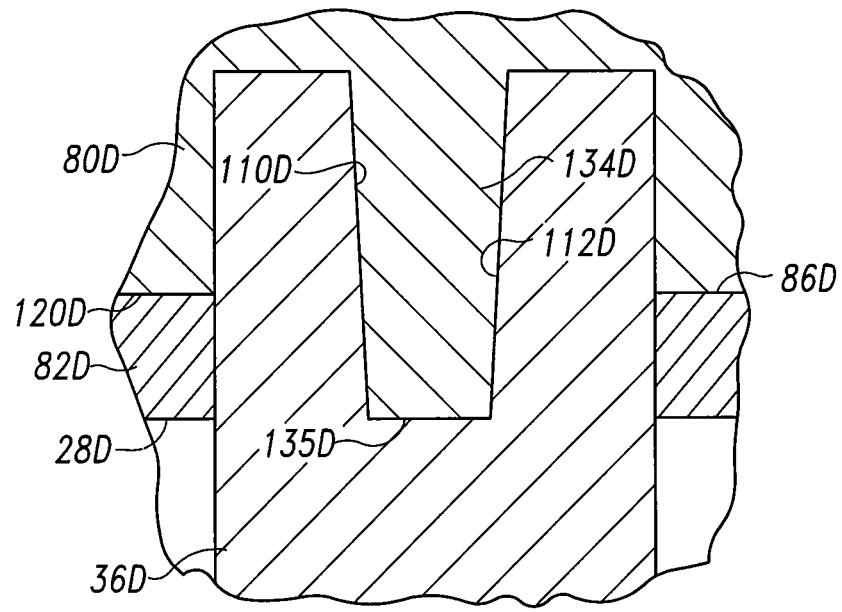
FIG. 30 is a cross-sectional view similar to FIG. 29, showing the proximal end of the peg preform mounted on the stud of FIG. 29.

In the embodiments of FIGS. 5, 7, 11, 18 and 20-23 the studs 134, 134 have free ends 135, 135A that do not extend beyond the plane of the distal surface 120, 120A of the solid metal portion 80, 80A of the tibial tray 14, 14A. An alternative embodiment of a tibial tray with longer studs is illustrated in FIGS. 28-30, where the same reference numbers have been used as those used in describing corresponding or similar parts in the embodiments of FIGS. 1 4-7, 11, 18 and 20-23 followed by the letter "D". In the embodiment of FIGS. 28-30, the free ends 135D of the studs extend beyond the plane of the distal surface 120D of the solid metal portion 80D of the tibial tray 14D. When assembled with the porous metal portion 82D as shown in FIGS. 28 and 30, the free ends 135D of the studs extend to the plane of the bone-engaging surface 28D of the porous metal portion of the tibial tray 14D.

In addition, it should be understood that the complementary mounting structures may be reversed, with the studs being present on the extensions and the complementary recesses being provided on the solid metal portion of the tibial tray.

The configuration of the proximal mounting surface 26, 26A of the solid metal portion 80, 80A of the tibial tray 14, 14A may vary depending on the type of implant. For example, if the prosthesis is a rotating platform type of mobile bearing knee prosthesis, the proximal mounting surface 26, 26A of the tibial tray 14, 14A and the distal mounting surface 19 of the bearing 16 will be smooth to allow for rotation of the bearing on the proximal mounting surface 26, 26A of the tibial tray 14, 14A. The embodiment illustrated in FIG. 1 is a fixed bearing design; the proximal mounting surface 26 of the tibial tray 14 and the distal mounting surface 19 of the bearing 16 in this illustration include complementary locking features that eliminate or at least minimize any relative movement between the bearing 16 and the tibial tray 14 when these components are assembled. These complementary locking features in the illustrated embodiment include pedestals 154, 158, tabs 160, 162 and recesses 178, 180 on the distal mounting surface 19 of the bearing 16 and buttresses 184, 186 and undercuts 194, 196, 198 on the proximal mounting surface 26 of the solid metal portion 80 of the tibial tray 14. Detailed descriptions of this and other designs for fixed bearing tibial trays may be found, for example, in the following U.S. patent applications, the disclosures of which are incorporated by reference herein in their entireties: U.S. Pat. No. 7,628,818, entitled "Fixed-Bearing Knee Prosthesis Having Interchangeable Components", filed on Sep. 28, 2007; U.S. patent application Ser. No. 11/860,833, entitled "Fixed-Bearing Knee Prosthesis", filed on Sep. 25, 2007 and published as US 20090082873 A1.

Preferably, the solid metal portion 80, 80A of the tibial tray 14, 14A is a solid metal preform, made from a standard titanium metal alloy. A suitable alloy for this purpose is Ti-6Al-4V. This alloy is advantageous in that it may be sintered to a porous metal portion made from commercially pure titanium powder. This same material may be used for the solid metal portion of the femoral component 12 as well. It should be understood that some of the advantages of the present invention may be achieved with other materials, such as a standard cobalt chrome molybdenum alloy; the present invention is not limited to any particular metal or alloy for the solid metal portions unless expressly called for in the claims.

Preferably, the porous metal portion 82, 82A of the tibial tray 14, 14A is a titanium metal foam. Such a foam may be made as taught in the following U.S. patent applications: U.S. Pub. No. 20080199720A1, U.S. Ser. No. 11/677,140, entitled "Porous Metal Foam Structures And Methods"; U.S. Pub. No. 20100098574A1, U.S. patent application Ser. No. 12/540,617 entitled "Mixtures For Forming Porous Constructs"; U.S. Pub. No. 20090326674A1, U.S. patent application Ser. No. 12/487,698 entitled "Open Celled Metal Implants with Roughened Surfaces and Method for Roughening Open Celled Metal Implants;" and U.S. Pub. No. 20090292365A1, U.S. patent application Ser. No. 12/470, 397 entitled "Implants with Roughened Surfaces"; the disclosures of all of the above patent applications are incorporated by reference herein in their entireties. The titanium metal powder used to make the porous metal portion 82, 82A may comprise commercially pure titanium powder (such as a titanium powder, 325 mesh (<45 um), produced by a hydride-dehydride process and that meets the ASTM F-1580 standard, available from Phelly Materials, Inc., Bergenfield, N.J., Part No. THD325 for example) or a mix of such a powder with a compatible titanium alloy powder, such as alloy Ti-6Al-4V. This material is advantageous in that it can be sintered to a titanium alloy such as Ti-6Al-4V. It is expected that other grades of commercially pure titanium may be used as well and that other powder metal materials may be available or developed in the future that can provide at least some of the advantages of the present invention; the present invention is not limited to any particular material unless expressly called for in the claims.

Although titanium foam is preferred, some of the advantages of the present invention may be achieved with alternative materials as well. One example of a suitable alternative material is tantalum porous metal, disclosed, for example in U.S. Pat. No. 5,282,861, entitled "Open Cell Tantalum Structures for Cancellous Bone Implants and Cell and Tissue Receptors," the disclosure of which is hereby incorporated by reference herein. Another example of an alternative is a solid metal body made from an implantable metal such as stainless steel, cobalt chrome alloy, titanium, titanium alloy or the like and with a porous coating disposed on both the bone-engaging surface and the surface engaging the polymer portion of the tibial tray. One type of porous coating which may be used as the porous portion 82, 82A of the tibial tray 14, 14A is Porocoat® porous coating which is commercially available from DePuy Orthopaedics of Warsaw, Ind. The porous metal preform 84A may be made using any of the process described in the above-cited patents and patent applications or through any standard process.

To make the tibial tray 14, 14A of the invention, the solid metal portion 80, 80A may be made as a solid metal preform by conventional methods, such as by casting, machining or some combination of casting and machining. Such processes may also be used to make a solid metal preform for the femoral component 12. For either the tibial tray 14, 14A or the femoral component 12, the recesses 122, 124, 126, 128, 130, 122A, 124A, 126A, 128A, 130A, and posts or studs 132, 134, 136, 138, 140, 132A, 134A, 136A, 138A, 140A may be machined into the solid metal preforms. For studs of the type illustrated in FIG. 21, threads may be formed in the studs 132, 134, 136, 138, 140 as well. For studs of the type illustrated in FIG. 22, the outer surface of the studs 132A, 134A, 136A, 138A, 140A may be shaped to define a Morse taper post.

It is expected that the articulation and mounting surfaces 18, 20, 26 of the solid metal portions of the femoral and tibial components 12, 14 may be treated to increase the lubricity, such as through Type II hard annodization.

The porous metal portion 82, 82A of the tibial tray 14, 14A and femoral component 12 may be made by molding the desired shape, using the processes described, for example, in U.S. Publication No. 20080199720A1; U.S. patent application Ser. No. 12/540,617 entitled "Mixtures For Forming Porous Constructs". Preforms so made can have, for example, a bulk porosity (or percent open area or void space) of from about 60% to about 85% (preferably about 65% to about 75%) as measured by volume, the forced intrusion of liquid mercury, and cross-section image analysis. This porosity/void space corresponds with a preform having a density of 15-35% (preferably 25-35%) of theoretical density for a similarly sized and shaped solid metal component. It should be understood that the porosity can be a product of various factors in the manufacturing process, such as the size of pore forming agent used. The resultant titanium metal foam may be treated to increase its roughness, such as by etching or blasting, as discussed in more detail below.

The molds used for preparing the porous metal portion 82A may be shaped so that the resultant product defines a single, integral porous metal preform 84A such as that illustrated in FIG. 16. Such a preform can be used to make a tibial tray 14A such as that illustrated in FIGS. 6-7. Alternatively, a plurality of molds may be provided to make individual and discrete extensions 30, 32, 34, 36, 38 and an individual and discrete base 85 for the embodiment of FIGS. 4-5 and 8-9. The bores 41, 43, 45, 47, 49, 41A, 43A, 45A, 47A, 49A in these components may be formed as part of the molding process or machined into the finished metal foam construct. For extensions of the type illustrated in FIGS. 5 and 9-12, threads may be formed in the walls defining the bores 41, 43, 45, 47, 49. For extensions of the type illustrated in FIGS. 7, 13-16 and 23, the walls defining the bores 41A, 43A, 45A, 47A, 49A may be tapered to define Morse taper bores.

The porous metal portion 82, 82A of the implant component and the solid metal portion 80, 80A of the implant component may then be assembled. For example, for an implant component of the type illustrated in FIGS. 6-7, the integral preform 84A may be pressed onto the distal surface 120A of the solid metal portion 80A, with the Morse taper studs 132A, 134A, 136A, 138A, 140A of the solid metal portion 80A pushed into the Morse taper bores 41A, 43A, 45A, 47A, 49A of the preform 84A, and with the annular raised portions 29A, 31A, 33A, 35A, 37A of the porous metal preform 84A received in the recesses 122A, 124A, 126A, 128A, 130A surrounding the studs 132A, 134A, 136A, 138A, 140A of the solid metal portion or preform 80A, as shown in FIGS. 7 and 22. The Morse taper frictional connection between the studs and the bores should hold the assembly together until sintering is complete. For an implant component of the type illustrated in FIGS. 4-5, each porous metal extension 30, 32, 34, 36, 38 may be individually assembled with the solid metal base 80 by threading the threaded bore 41, 43, 45, 47, 49 of each porous metal extension 30, 32, 34, 36, 38 onto the threaded stud 132, 134, 136, 138, 140 of the solid metal portion or preform 80 until the annular end of the extension is received in the recess 122, 124, 126, 128, 130 surrounding the stud 132, 134, 136, 138 as shown in FIG. 11. This threaded connection between the studs 132, 134, 136, 138 and the bores 41, 43, 45, 47, 49 should hold the assembly together until sintering is complete. It should be understood that the Morse taper connection and threaded connection described above are two examples of complementary structures for connecting the porous metal extensions to the solid metal portion of the tray; those skilled in the art will recognize that other types of connections may be used.

The assembly of the solid metal portion 80, 80A, 81 and the porous metal portions 82, 82A, 83 may then be sintered together to form the final tibial tray 14, 14A or femoral component 12. Sintering may be accomplished utilizing the same temperatures and times used to form the porous metal portion. For example, as disclosed in U.S. Pub. No. 20080199720A1, the assembly may be sintered under the following conditions to form the final implant component: heating at temperatures of from about 2100° F. to about 2700° F. (preferably about 2500° F.) for about 2 hr to about 10 hr (preferably about 3 hr to about 6 hr). The sintered part may then be cooled following an appropriate cooling cycle.

For both the femoral and tibial components, once assembled, the porous metal portion 82, 82A, 83 defines the bone-engaging surfaces 13, 15, 28, 28A of the implant component 12, 14, 14A. In addition, for both the femoral and tibial components, the solid metal portions 80, 80A, 81 contact the bearing 16, both on the mounting side 19 and the articulation side 17.

As mentioned above, in some situations, it may be desirable to treat the porous metal portion 82, 82A, 83 to selectively increase the roughness of some or all of the bone-engaging surfaces. The porous metal portion 82, 82A, 83 may be treated through etching or blasting, for example, to increase the roughness of the outer surface, as disclosed, for example in U.S. Pub. No. 20090326674, U.S. patent application Ser. No. 12/487,698 entitled "Open Celled Metal Implants with Roughened Surfaces and Method for Roughening Open Celled Metal Implants," and U.S. Pub. No. 20090292365A1, U.S. patent application Ser. No. 12/470,397 entitled "Implants with Roughened Surfaces." Although the etching and blasting techniques disclosed in those patent applications are advantageous for use with titanium metal foams, it should be understood that the techniques disclosed in these patent applications are provided as examples only; the present invention is not limited to roughened porous metal or to any particular roughening technique unless expressly called for in the claims. The disclosures of these patent applications are incorporated by reference herein in their entireties. Such roughening is expected to make the treated surfaces more conducive to bone ingrowth to improve ultimate fixation of the components.

One application of the etching and blasting roughening techniques of the above-identified patent applications is to roughen the porous metal portions 82, 82A, 83 of the tibial tray 14, 14A and femoral component 12. In addition, it may be advantageous to selectively roughen certain surfaces of the porous metal portion 82, 82A, 83 while leaving other surfaces in their as-machined state, with lower roughnesses, or while further treating these other surfaces to decrease the roughness of these other surfaces. Specifically, to facilitate removal of either the tibial tray 14, 14A or the femoral component 12 from the bone in revision surgery, it may be desirable to discourage bone ingrowth at the distal ends 40, 42, 44, 46, 48, 40A, 42A, 44A, 46A, 48A of the tibial extensions and proximal ends 51 of the femoral extensions 39. This may be accomplished by selectively roughening the distal bone-engaging surface 28, 28A of the platform and the outer surfaces of the extensions 30, 32, 34, 36, 38, 30A, 32A, 34A, 36A, 38A at the junctions 60, 62, 66, 69, 60A, 62A, 66A and adjacent surfaces while leaving the ends 40, 42, 44, 46, 48, 40A, 42A, 44A, 46A, 48A opposite the junctions 60, 62, 66, 69, 60A, 62A, 66A (and some adjacent surfaces if desired) in the as-machined state.

A variety of other techniques are known for treating porous metal implants and may be applied to the present invention. For example, calcium phosphate coatings (such as hydroxyapatite) may be applied to some or all of the porous portions of the embodiments of the present invention, with or without additional therapeutic agents, as disclosed in U.S. Pat. Pub. No. 20060257358 entitled "Suspension Of Calcium Phosphate Particulates For Local Delivery Of Therapeutic Agents." Alternatively, electrophoretic deposition of a material such as calcium phosphate may be used.

Alternatively, or additionally, the surfaces of the porous metal portion 82, 82A where bone ingrowth is undesirable may be machined, milled, polished or otherwise smoothed to reduce the roughness and/or porosity of the surface. Machining, milling, polishing or smoothing can be expected to close some or all of the pores and change the surface profile, thereby lowering the coefficient of friction along the surface. For example, the surfaces where bone ingrowth is undesirable may be machined with a standard carbide tip rotating at a standard speed, such as 600 rpm. Machining may be carried on until the surface is smeared and has a solid rather than porous appearance; about 0.015 inches of material may be removed in this process. It should be understood that a commercial manufacturing process may be run under different parameters. Machining, milling, polishing or smoothing can be accomplished when the component is in the green state, before sintering, after sintering, or both before and after sintering.

Alternative methods of producing surfaces with lower surface roughnesses and lower static coefficients of friction may be used. For example, pores may be selectively filled with metal. As another alternative, when molding the porous metal portion of the implant or the pegs and stem, or when sintering the solid metal and porous metal portions together, solid metal pieces may be sintered to the free ends of the pegs and stems. Another alternative would include molding a non-porous biocompatible polymer cap to the ends of the extensions; an example of such a polymer is polyetheretherketone (PEEK).

Thus, various techniques are available for selectively roughening, smoothing and changing the porosity of surfaces of the porous metal portions of the implants.

The porosity and roughness of other surfaces may also be modified. Considering the embodiment of FIGS. 1 and 3, for example, there are surfaces of the porous metal portion 82 that are not intended to engage bone or another part of the implant component. An example of such a surface is exposed peripheral surface 150 of the porous portion 82 of the tibial tray 14. This exposed peripheral surface 150 extends generally perpendicularly from the distal bone-engaging surface 28 to the upper surface 86 of the porous base 85 in the embodiment of FIGS. 1, 3 and 5. At least some of this exposed peripheral surface can be expected to be engaged by soft tissue when implanted. If this exposed peripheral surface is rough, adjacent soft tissue could be irritated when the tray is implanted. Accordingly, it may be preferable to smooth these exposed peripheral surfaces, or any surface that may engage soft tissue instead of bone or another portion of the implant. Any of the smoothing methods described above could be used. For example, the exposed peripheral surfaces could be machined with a carbide bit as described above.

The surfaces, including those that are roughened, smoothed or those without any treatment, can be characterized in various ways, such as by determining the static coefficient of friction or by characterizing the surface profile or surface roughness under ISO 4287 (1997).

First, with respect to the static coefficient of friction, U.S. Pub. No. 20090292365A1 (U.S. patent application Ser. No. 12/470,397) discloses that porous metal samples (both commercially pure titanium and Ti-6Al-4V) were machined in the green state. Friction tests were performed using a "sled on a plane" method. The "sled" consisted of the 0.75 in×0.75 square metallic matrix samples. Each "plane" was a polymer bone analog comprising a milled sample of Last-A-Foam® 6720 (General Plastics Manufacturing Company, Tacoma, Wash.), a rigid, closed-cell polyurethane foam with a density of 20 lb/ft$^3$. Each sled was connected to a 250 N load cell by 10 lb monofilament line and pulled at 10 mm/min for 0.8 in. A weight was placed on the sled to create a normal force of 30 N. The static friction coefficient was calculated from the maximum force recorded before the first 0.5 N drop in force.

The static coefficients of friction with polymer bone analogs for the surfaces were found to be 0.52 for commercially pure titanium that was machined in the green state and 0.65 for Ti-6Al-4V that was machined in the green state, with standard deviations of 0.1. In contrast, porous metal components of the same materials that were blasted as taught in U.S. Pub. No. 20090292365A1 (U.S. patent application Ser. No. 12/470,397) had average static coefficients of friction with polymer bone analogs of 0.72-0.89 for commercially pure titanium and 1.09-1.35 for Ti-6Al-4V.

Thus, a tibial tray made according to this aspect of the invention may have a stem 30, 30A and pegs 32, 34, 36, 38, 32A, 34A, 36A, 38A with distal surfaces 40, 42, 44, 46, 48, 40A, 42A, 44A, 46A, 48A having a coefficient of static friction (with a polymer bone analog comprising rigid closed-cell polyurethane foam with a density of about 20 lb/ft$^3$) less than 0.7; the outer surfaces of these pegs 32, 34, 36, 38, 32A, 34A, 36A, 38A and stem 30, 30A near the junctions 60, 62, 66, 60A, 62A, 66A may have coefficients of static friction (with a polymer bone analog comprising rigid closed-cell polyurethane foam with a density of about 20 lb/ft$^3$) of more than 0.7. For pegs 32A, 34A, 36A, 38A of the type illustrated in FIGS. 7, 12-14 and 16, the flat distal surface 42A, 44A, 46A, 48A may have a lower coefficient of friction; for an extension of the type illustrated in FIGS. 1, 3-5 and 9, all or part of the spheroidal distal end may have a lower coefficient of friction. Similar results are expected to be obtained with selective etching of the extensions. Next considering the surface profile and surface roughness characteristics under ISO 4287 (1997), samples were made from commercially pure titanium metal powder (commercially pure titanium powder, 325 mesh (<45 um), produced by a hydride-dehydride process and that meets the ASTM F-1580 standard, purchased from Phelly Materials, Inc., Bergenfield, N.J., Part No. THD325) and produced using the process described in U.S. Publication No. 20080199720A1 (U.S. patent application Ser. No. 11/677,140). The space filler used in making the samples was salt (425-600 micron NaCl). The commercially pure titanium metal powder and salt were mixed, compacted and green-machined. The salt was dissolved out of the machined samples and the samples were then dried. Some of the samples were set aside for surface characterization without sintering. Some of the samples were then sintered. Some of the samples were salt blasted in the green condition using salt (<250 micron NaCl) using the process described in U.S. Pub. No. 20090292365A1 (U.S. patent application Ser. No. 12/470, 397) and then sintered. Of the sintered samples that were not salt blasted, some of the samples were lightly polished on 400 sanding grit paper and some of the samples were milled after sintering using a milling machine. Some of the sintered samples were SiC ground. Some of the sintered samples were turned on one of the lathes available in the assignee's research laboratory, and some were turned on one of the lathes available in the assignee's production facility.

The surfaces of the samples were then characterized using a contact surface profilometer according to ISO 4287 (1997). The characterizations were performed using a Zeiss Surfcomm 5000 contact profilometer with a 2 micron radius ruby ball; the measurement speed was 0.3 mm/sec; the tilt correction was least square straight.

For some of the samples, results were recorded using the "P" values from ISO 4287 (1997). For some of the samples, results were recorded using both the "P" values and "R" values from ISO 4287 (1997). As there described, the "P" values are the primary profile parameters (reference is made to ISO 3274, which defines the primary profile as the "Total profile after application of the short wavelength filter, ks.") and include both roughness and waviness as components of the primary profile; the "R" values are roughness parameters. ISO 3274 and ISO 4287 are incorporated by reference herein in their entireties.

Figure 40A:
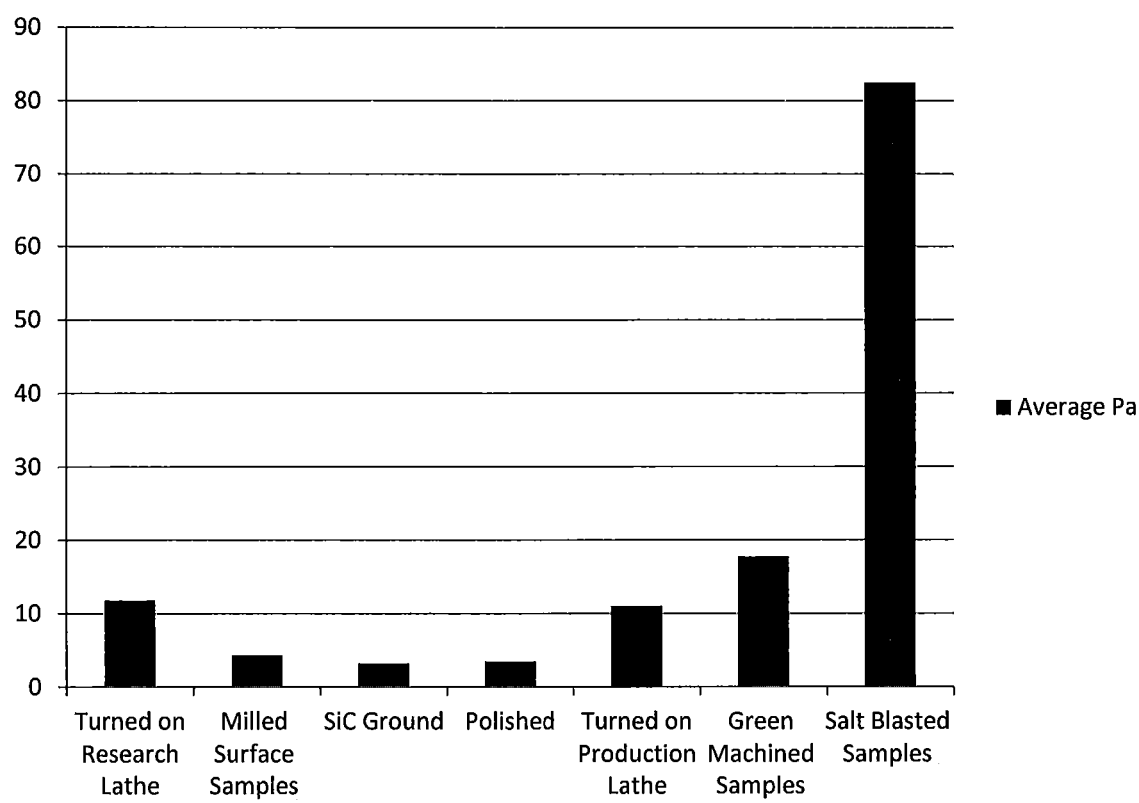
FIG. 40A is a bar graph comparing average Pa surface profile values for the titanium foam metal samples set forth in FIGS. 33A, 34A, 35A, 36A, 37A and 38A.
Figure 40B:
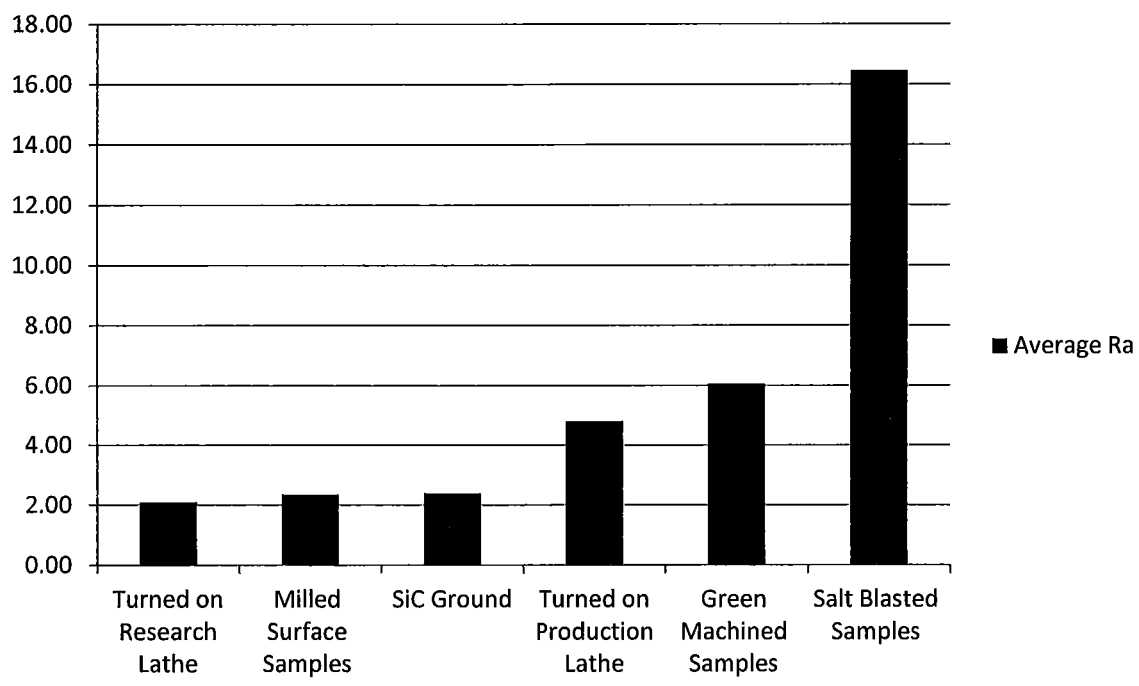
FIG. 40B is a bar graph comparing average Ra surface roughness values for the titanium foam samples set forth in FIGS. 33B, 34B, 35B, 36B, 37B and 38B.

The results of these surface characterizations are shown in FIGS. 33A-39. Primary profile parameters are shown in FIGS. 33A, 34A, 35A, 36A, 37A, 38A and 39. The column headings starting with the letter "P" (Pa, Pq, Pp, Pv, Pc.1, PDq, Psk, Pku and Pt) all refer to surface profile parameters as defined in ISO 4287 (1997). Roughness parameters are shown in FIGS. 33B, 34B, 35B, 36B, 37B and 38B. The column headings starting with the letter "R" (Ra, Rz, Rp, Rpmax, Rv and Rt) all refer to surface roughness parameters under ISO 4287 (1997). FIG. 40A is a bar graph illustrating the differences in the average value of the parameter Pa for the green machined, salt blasted, milled, ground, and polished samples, as well as the samples turned on different lathes. FIG. 40B is a bar graph illustrating the differences in the average value of the roughness parameter Ra for the green machined, salt blasted, milled, and ground samples, as well as the samples turned on different lathes. As can be seen from FIGS. 40A and 40B, the Pa and Ra values of the titanium foam samples can be significantly reduced from the green machined state by milling, grinding and/or polishing the titanium foam, as well as be turning the foam on a lathe. The results are more dramatic when comparing the surface profiles and roughnesses to those of the sale blasted samples.

The results for some of the surface profile parameters are also provided in U.S. Pub. No. 20090292365A1 (U.S. patent application Ser. No. 12/470,397). As there shown the Pa, Pp, Pt and Pq values (as defined in that patent application) for the samples all at least doubled for the blasted samples as compared to the machined samples with no blasting.

Since the surfaces of the milled and polished titanium foam samples have lower Pa and Ra values, it is expected that the milled, ground and polished titanium foam samples would have static friction coefficients with polymer bone analogs less than 0.52+/−0.1 for commercially pure titanium and 0.65+/−0.1 for Ti-6Al-4V.

The coefficient of static friction of such a surface is expected to be no greater than those reported in U.S. Pub. No. 20090292365A1 (U.S. patent application Ser. No. 12/470,397) for metal foam samples machined in the green state and not subjected to any roughening treatment (0.52 for commercially pure titanium and 0.65 for Ti-6Al-4V, with standard deviations of 0.1). Profile parameters of the peripheral exposed surfaces are also expected to be no greater than the Pa, Pp, Pt and Pq values (as defined in U.S. Pub. No. 20090292365A1, U.S. patent application Ser. No. 12/470, 397) for the metal foam samples machined in the green state. It is anticipated that the machining parameters could be adjusted to optimize the surface finishes of the peripheral exposed surfaces and distal surfaces 40. The exposed porous metal surfaces perpendicular to the bone-engaging surfaces of the femoral component 12 may be similarly treated.

An additional effect of smoothing the exposed peripheral surfaces is that the pores will tend to be closed, as discussed above. Reducing the porosity of the exposed peripheral surfaces can be advantageous: if the resected bone bleeds through into the body of the porous metal portion of the implant, the blood will not bleed through the exposed peripheral surfaces into the joint space, thereby eliminating any problems associated with blood in the joint space.

Figure 31:
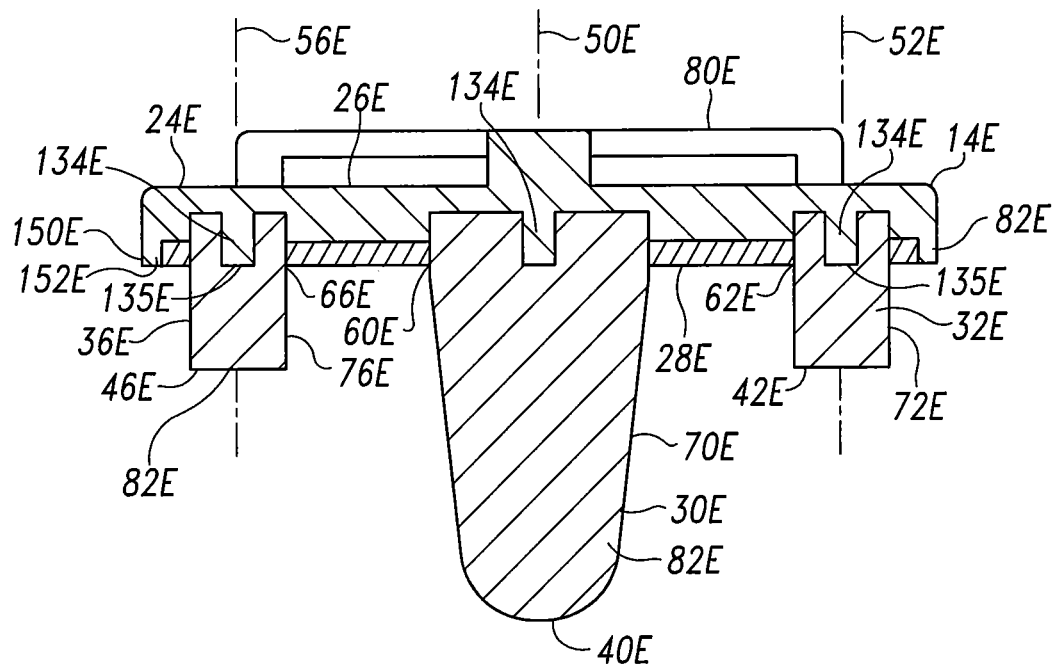
FIG. 31 is a cross-sectional view similar to FIGS. 5, 7 and 28, of an alternative embodiment of a tibial tray that may be used in the present invention.

There are alternative ways of substantially reducing surface roughness of implant surfaces that may come into contact with soft tissue. For example, in the tibial tray illustrated in FIG. 31 (where the same reference numbers have been used as those used in describing corresponding or similar parts in the embodiments of FIGS. 1 4-7, 11, 18 and 20-23 followed by the letter "E"), the periphery of the solid metal portion 80E includes a rim 152E that extends to the plane of the bone-engaging surface 28E. In this embodiment, the rim 152E defines a pocket in which the porous metal base 85E is received so that the exposed peripheral surface 150E comprises solid metal. In this embodiment, the tibial tray may be made from a base component, such as a cast component, with pockets configured for cemented fixation, and the pockets could be filled with porous metal, such as a titanium foam, and then sintered.

Figure 32:
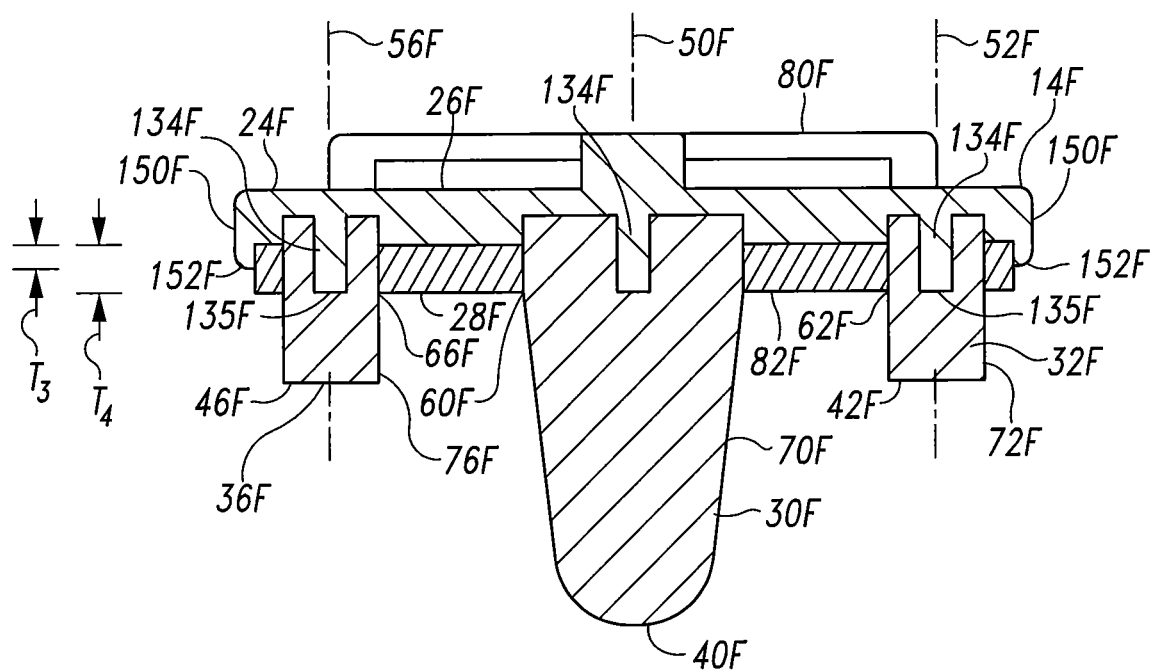
FIG. 32 is a cross-sectional view similar to FIGS. 5, 7, 28 and 31, of an alternative embodiment of a tibial tray that may be used in the present invention.

FIG. 32 illustrates another alternative embodiment of a tibial tray (where the same reference numbers have been used as those used in describing corresponding or similar parts in the embodiments of FIGS. 1 4-7, 11, 18, 20-23 and 31 followed by the letter "F"). In this embodiment, the periphery of the solid metal portion 80F includes a rim 152F that extends to a plane above the plane of the bone-engaging surface 28F. In this embodiment, the rim 152F defines a pocket in which a portion of the porous metal base 85F is received. In this embodiment, the porous metal base 85F is recessed from the periphery of the tibial tray to eliminate contact between the porous metal and soft tissue. Thus, the exposed peripheral surface 150F comprises solid metal. In this embodiment, the tibial tray may be made from a base component, such as a cast component, with pockets configured for cemented fixation, and the pockets could be filled with porous metal, such as a titanium foam, and then sintered. The pockets defined by the rim 152F have a depth shown at $T_3$ in FIG. 32, and the porous metal base 85F has a thickness shown as $T_4$ in FIG. 32. $T_4$ is greater than $T_3$ to ensure that the bone-engaging surface 28F stands proud to thereby ensure that the surface 28F fully engages and transfers load to the underlying bone.

Other surfaces of the porous metal component or portion may be advantageously smoothed. The inventors have found that the strength of the bonding in such sintered assemblies of porous titanium preforms onto a dense titanium substrate is improved when the mating titanium foam surface is machined in a way to smear or close the surface porosity. For example, upper surfaces 86, 86A of the preforms 85, 85A may be smoothed by machining prior to sintering the preforms to the solid metal portions 80, 80A to make the tibial trays 14, 14A.

To characterize the differences in the strengths of the bonds between solid metal and metal foams with different surface characteristics, two foam ring groups were prepared using as-received −325 mesh irregular unalloyed titanium powder (commercially pure titanium powder, as described above). For both foam ring groups, the titanium powder was weighed and combined with granular NaCl space holders that had been sieved into a nominal size range of 425-600 μm in a weight ratio to give 80.5% volume fraction NaCl particles. The Ti powder and NaCl space holders were mixed, and the mixture was filled into flexible molds and compacted in a cold isostatic press. The compressed parts were machined in the green state. The NaCl space holder was then dissolved in water and the parts dried.

After the foam parts were dried, they were pre-sintered in vacuum at a temperature of 2500° F. for 4 hours. A hole was then machined through the axial center of each titanium foam part and the foam parts were then assembled with a line-to-line to slight press fit to pins cut from as-received, ½ inch, wrought Ti-6Al-4V titanium alloy bar. The assemblies were then sintered in vacuum for 4 hours at sintering temperature for 8 hours total time.

The common aspects of the processing of the assembly of the titanium foam and solid titanium alloy parts is summarized in the following table:

| Group | Foam Powder Material | Space Holder Nominal Size (μm) | Volume Fraction NaCl (%) | Sinter Temp (° F.) | Sinter Time (hr) |
|---|---|---|---|---|---|
| 1 | CP Ti | 425-600 | 80.5 | 2500 | 4 + 4 |
| 2 | CP Ti | 425-600 | 80.5 | 2500 | 4 + 4 |

The Group 1 samples differed from the Group 2 samples in the manner in which the holes were machined into the rings. The machining processes are summarized in the following table:

| | Nominal Specimen Dimensions (mm) | | | | Foam Through Hole Machining | | |
|---|---|---|---|---|---|---|---|
| Group | Foam Through Hole Dia. | Pin Dia. | Foam Length | Foam OD | Speed (rpm) | Feed (in./revo-lution) | Tool Radius (in.) |
| 1 | 12.65 | 12.68 | 5 | 17.25 | 640 | 0.003 | 0.015 |
| 2 | 12.62 | 12.68 | 5 | 17.23 | 1000 | 0.004 | 0.030 |

The machining process for Group 1 smeared or closed the porosity of the samples, while the machining process for Group 2 retained a more open surface porosity. Ring shear samples were also prepared for determination of the extent of titanium foam to substrate bonding by image analysis of metallographically mounted and polished cross sections. Although not measured in this example, it is expected that the coefficient of static friction, primary profile parameters (P values) and roughness values of the Group 1 samples are less than the coefficient of static friction, primary profile parameters (P values) and roughness values of the Group 2 samples.

The samples were then tested for shear strength. Testing was performed on an MTS Alliance RF/100 test frame with a 50 kN load cell to which an MTS load platen was attached. A custom made ring shear fixture was attached to the base of the test frame. The fixture had a through hole which provided a small clearance from the test specimen pin diameter. The test specimen was inserted into the through hole until the foam ring contacted the face of the fixture. The specimen was centered within this through hole and the assembly centered under the MTS platen. The MTS was commanded to move the crosshead downward to shear the foam ring from the pin at 0.1 inch/minute until the peak load was detected. Data was acquired and the stress and strain at 0.2% offset yield and the peak stress were calculated using MTS TestWorks 4.08B software.

Figure 41:
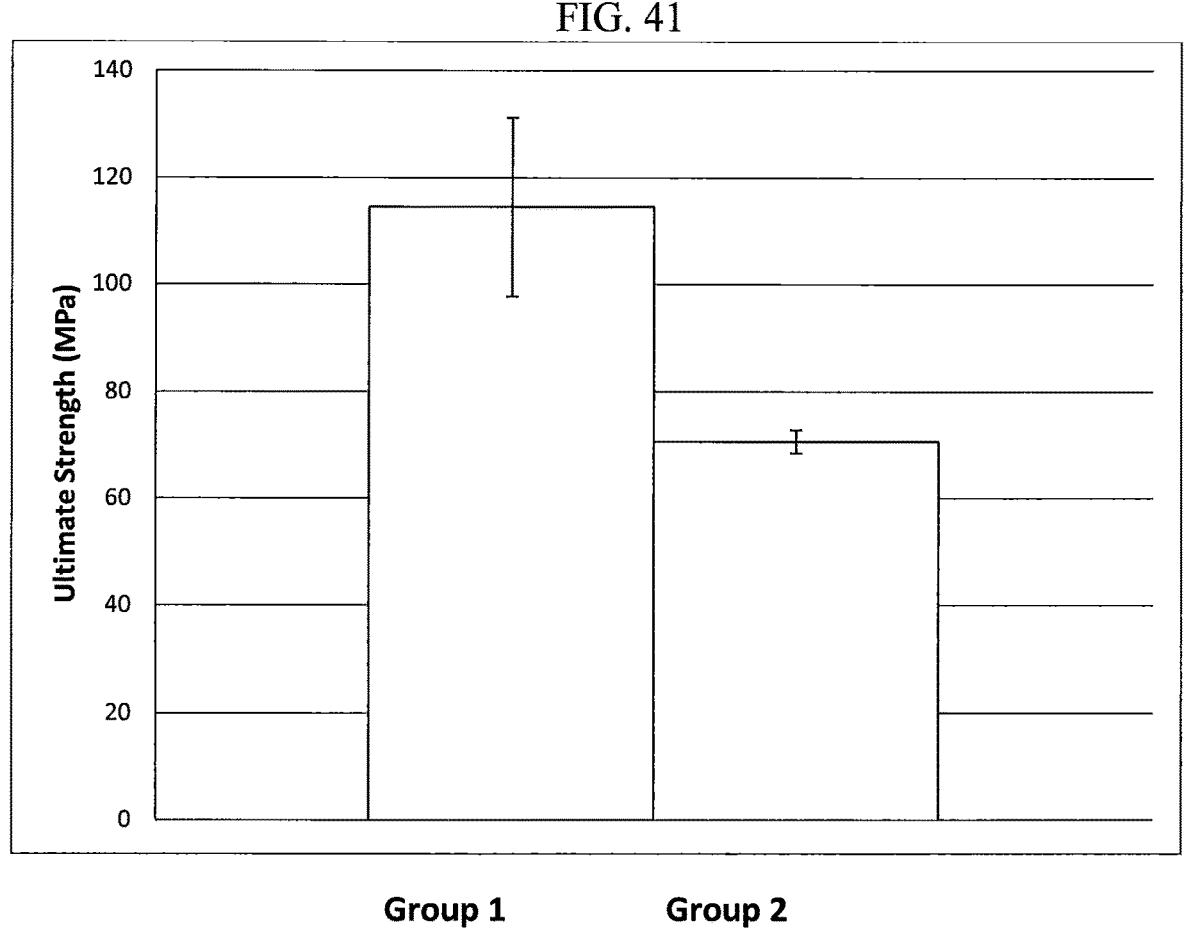
FIG. 41 is a bar graph comparing the shear strength for samples of solid metal and porous metal assemblies sintered together, illustrating the effect of the varying the machining parameters used in preparing the surface of the porous metal portion that contacts the solid metal portion, with error bars indicating standard deviation.
Figure 42A:
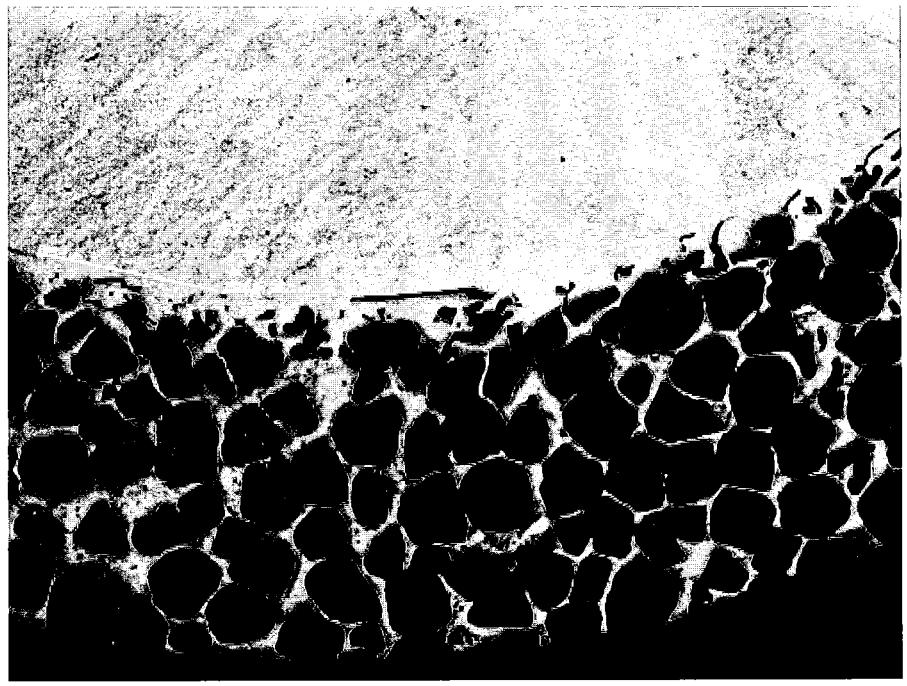
FIG. 42A is an image of a cross sectioned ring shear specimen showing the extent of bonding when the mating inside diameter on a titanium foam ring was machined in a way that smeared the surface porosity.
Figure 42B:
FIG. 42B is another image of a cross sectioned ring shear specimen showing the extent of bonding when the mating inside diameter on a titanium foam ring was machined in a way that smeared the surface porosity.
Figure 42C:
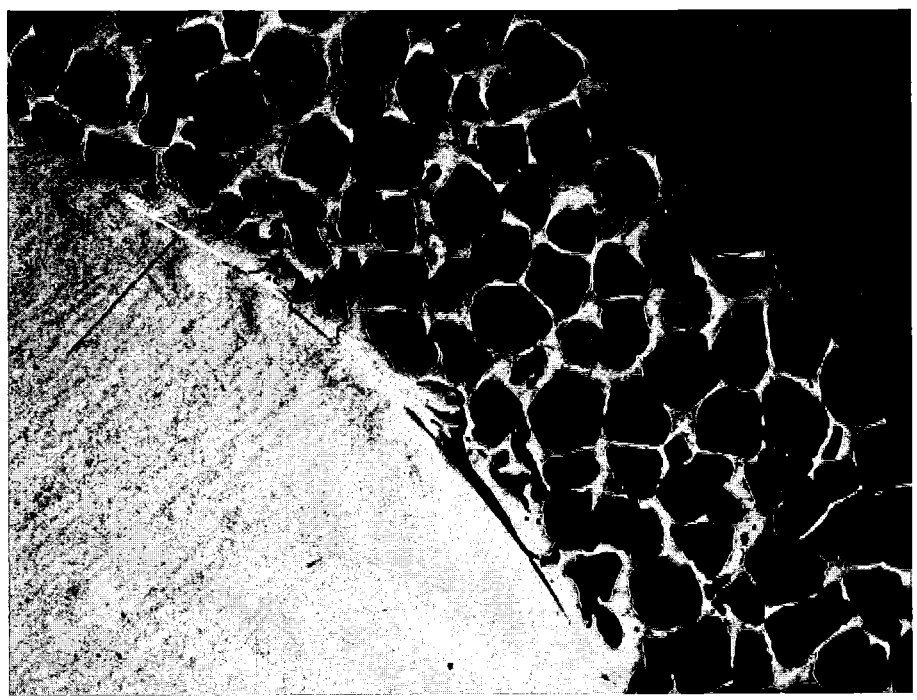
FIG. 42C is another image of a cross sectioned ring shear specimen showing the extent of bonding when the mating inside diameter on a titanium foam ring was machined in a way that smeared the surface porosity.
Figure 43A:
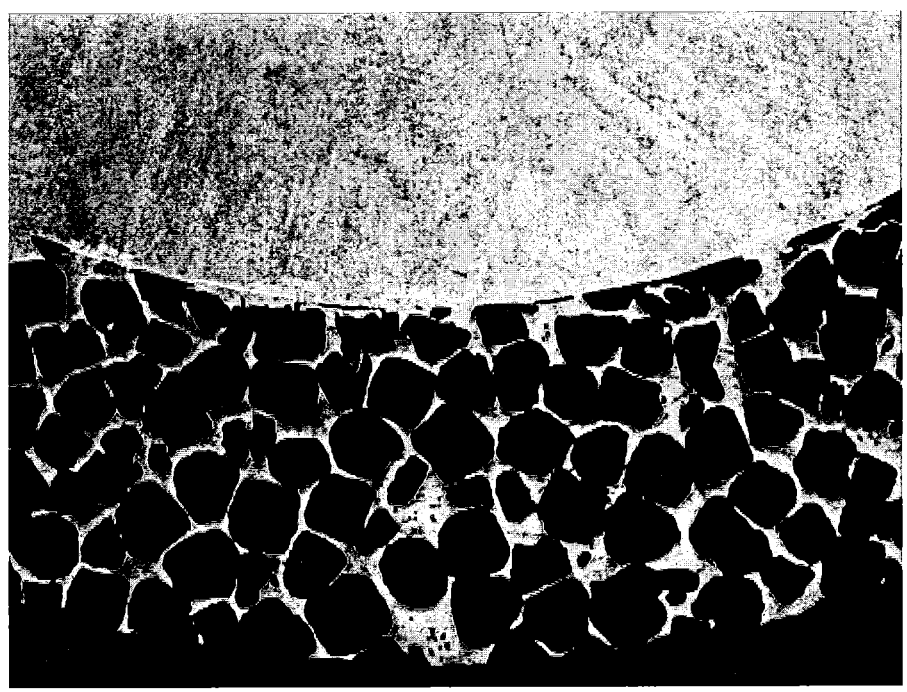
FIG. 43A is an image of a cross sectioned ring shear specimen showing the extent of bonding when the mating inside diameter on a titanium foam ring was machined in a way that maintained open surface porosity.
Figure 43B:
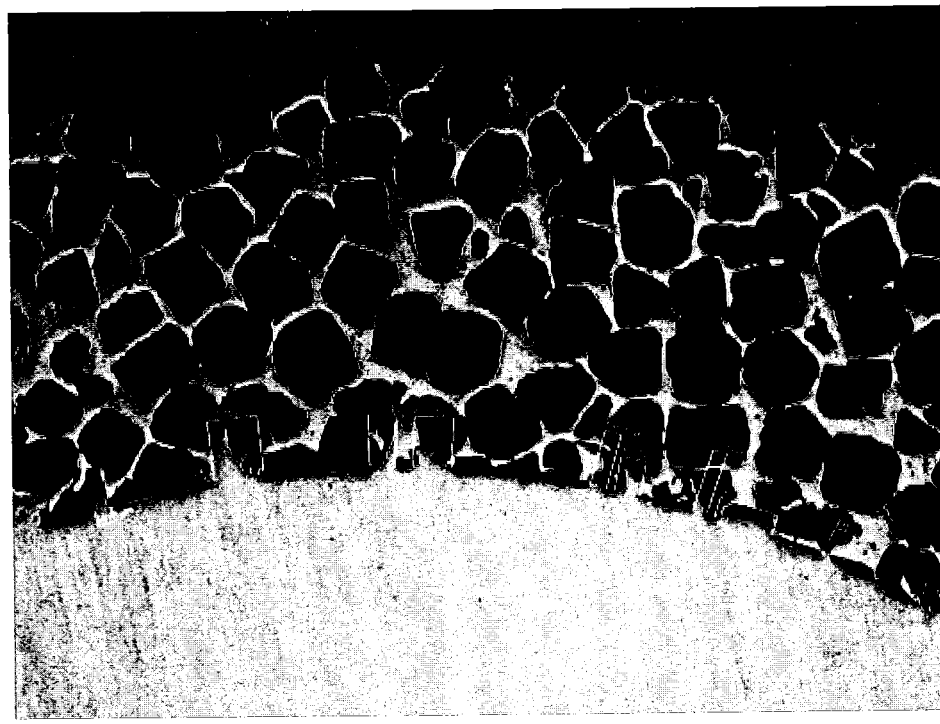
FIG. 43B is another image of a cross sectioned ring shear specimen showing the extent of bonding when the mating inside diameter on a titanium foam ring was machined in a way that maintained open surface porosity.
Figure 43C:
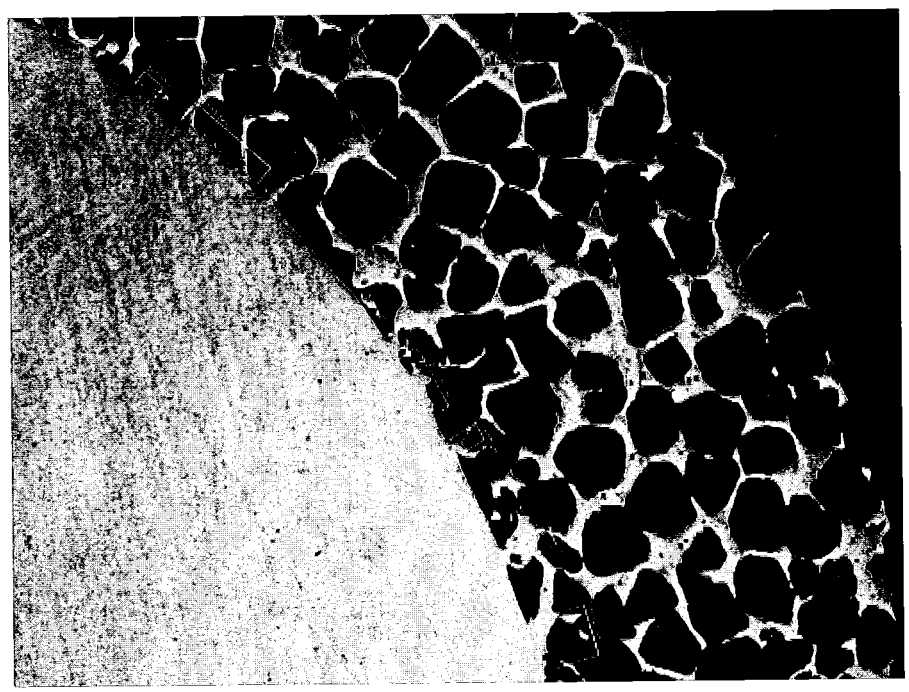
FIG. 43C is another image of a cross sectioned ring shear specimen showing the extent of bonding when the mating inside diameter on a titanium foam ring was machined in a way that maintained open surface porosity.

FIG. 41 illustrates that the porous metal-solid metal bond in the Group 1 samples had greater shear strength than the porous metal-solid metal bond in the Group 2 samples. Representative mounted and polished cross-sectional images of the Group 1 and Group 2 samples are provided in FIGS. 42 and 43, which illustrate that the length of the bonded interface between the porous metal portion and the solid metal portion is greater in the Group 1 samples than in the Group 2 samples.

Thus, it may be advantageous to decrease the porosity, static coefficient of friction and surface roughness of: surfaces that may be contacted by soft tissue; surfaces that are difficult to access during a revision procedure; and surfaces that will form a bond with a solid metal portion of an implant component. In other surfaces where bone ingrowth is desirable, surface roughness and static coefficient of friction may be maintained or increased by roughening.

The principles of the present invention may be applied to other implant components as well. Bone loss on the proximal tibia or distal femur can make it difficult to properly position and support the tibial component 14, 14A or femoral component 12 of the implant system 10 on the bone surface. The prior art has addressed this problem through the use of wedges or augments. Generally, the wedge or augment is placed between part of the bone-engaging surface of the implant component and part of the bone to support part of the implant component on the bone by augmenting part of the bone.

Due in part to the fact that the size, shape and anatomy of virtually every patient is different, and the variability in the location and amount of bone loss on the proximal tibia, an extensive number of a variety of wedges and augments have been made available to the orthopedic surgeon. For example, a typical surgical kit will include tibial wedges of different thicknesses and different configurations for use on either the medial or the lateral sides of the tibial.

In the present invention, the prosthetic knee system or kit 10 may include wedges or augments for both the femoral and tibial sides of the system. These augments may comprise porous metal, and more particularly, a porous metal foam of the same material and made under the same conditions as those discussed above for the porous metal portions 82, 82A, 83 of the tibial trays 14, 14A and femoral components 12.

For the femoral side, augments may have features such as those disclosed in the following U.S. Pat. Nos. 6,005,018 and 5,984,969, which are incorporated by reference herein in their entireties. For the tibial side, augments may have features such as those disclosed in U.S. Pat. Nos. 7,175,665 and 5,019,103, which are incorporated by reference herein in their entireties.

Figure 24:
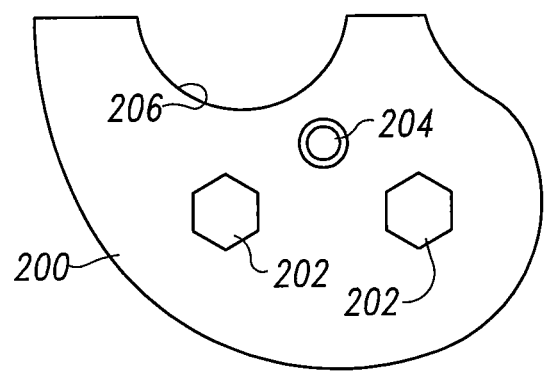
FIG. 24 is a bottom plan view of a tibial augment that may be used with the present invention.
Figure 25:
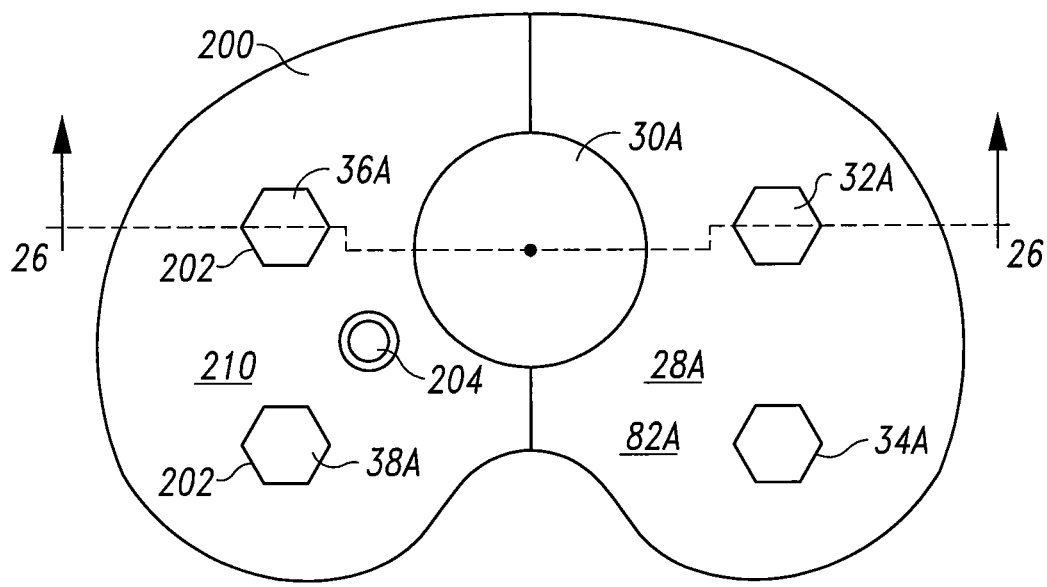
FIG. 25 is a bottom plan view of the tibial augment of FIG. 24 assembled with a tibial tray similar to that shown in FIGS. 6-7.
Figure 26:
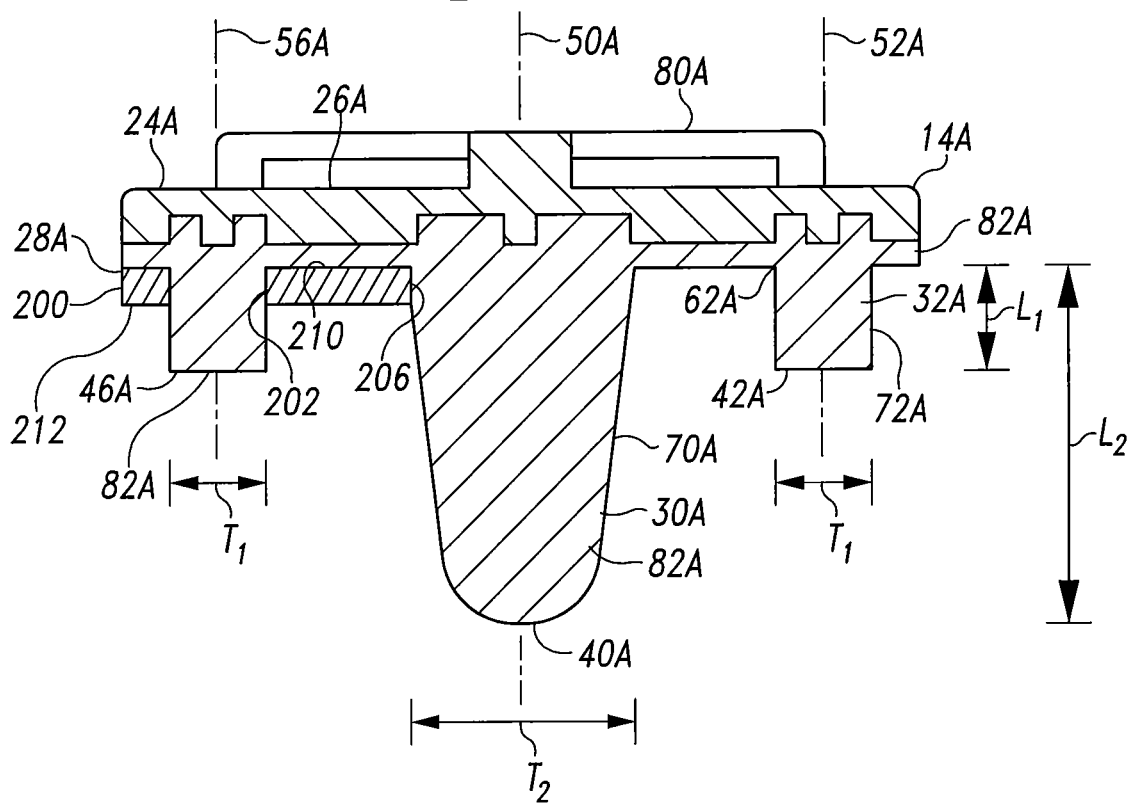
FIG. 26 is a cross sectional view of the assembly of FIG. 25, taken along line 26-26 of FIG. 25, as viewed in the direction of the arrows.

An illustrative tibial augment is shown in FIG. 24 at 200. The illustrated tibial augment 200 is made of porous metal across its entire length, width and thickness. The augment 200 includes through-bores 202 sized and shaped to receive portions of pegs or extensions (such as pegs 32, 34, 36, 38, 32A, 34A, 36A, 38A) that may be present, and may be mounted to the porous metal portion 82, 82A of the tibial tray as illustrated in FIGS. 25-26. Frictional engagement of the augment and the pegs or extensions and the porous metal portion of the tray may be sufficient to fix the augment to the tray; otherwise, the augment 200 may include additional through-bores sized and shaped to receive screws (not shown) for fixing the augment 200 to the tibial tray 14, 14A; an illustrative through bore is shown at 204 in FIGS. 24-25. The augment 200 may also include a recess such as recess 206 to accommodate any stem (such as stem 30, 30A) on the tibial tray 14. Complementary blind bores may be provided in the tibial tray to receive parts of the screws. The bores in the tibial tray may be threaded, and may be provided in the porous metal portion 82, 82A or may extend through the porous metal portion 82, 82A and into the solid metal portion 80, 80A. The surfaces defining the through-bores 202, 204 in the augments may be smooth (i.e., non-threaded) and the through-bores 204 for the screws may have top and bottom countersinks so that the augment may be used on either the medial or lateral side, as disclosed in U.S. Pat. No. 7,175,665. As shown in FIG. 26, when the augment is mounted on the tibial tray 14A, one surface 210 of the augment bears against distal surface 28A of the porous metal portion 82A of the tibial tray 14A and the opposite surface 212 of the augment 200 becomes the bone-engaging surface of this side of the tibial tray 14A.

The augment 200 may comprise a porous metal foam. For example, the augment 200 may be made according to the processes disclosed in the following U.S. patent applications: U.S. Publication No. 20080199720A1 (U.S. Ser. No. 11/677,140), filed on Feb. 21, 2007 and entitled "Porous Metal Foam Structures And Methods"; U.S. patent application Ser. No. 12/540,617 entitled "Mixtures For Forming Porous Constructs"; U.S. patent application Ser. No. 12/487, 698 DEP5922USNP) entitled "Open Celled Metal Implants with Roughened Surfaces and Method for Roughening Open Celled Metal Implants;" and U.S. Pub. No. 20090292365A1 (U.S. patent application Ser. No. 12/470,397) entitled "Implants with Roughened Surfaces." Exposed peripheral surfaces of the augments, such as surface 250 in FIGS. 25 and 26, may be treated to smooth the exposed peripheral surface 250. The smoothing treatment may comprise, for example, machining as discussed above; alternatively or in addition, the surface 250 may be masked during any process used to roughen other surfaces of the augment.

To use the system of the present invention, the surgeon would prepare the distal femur and proximal tibia to receive the bone implants 12, 14, 14A using conventional techniques and implant the tibial tray and femoral component using conventional techniques for cementless components. The tibial bearing 16 is typically assembled with the tibial tray 14, 14A after the tray 14, 14A has been implanted.

After implantation, it is anticipated that bone will grow into the porous metal portion 82, 82A of the tibial tray 14, 14A and porous metal portion 83 of the femoral component 12, including the pegs 32, 34, 36, 38, 39, 32A, 34A, 36A, 38A and stem 30, 30A. If the pegs and stem are made with smoother free ends 40, 42, 44, 46, 48, 51, 40A, 42A, 44A, 46A bone will not, however, grow or grow as vigorously into the smoother free ends. Thus, it is anticipated that there will be bone ingrowth into the distal surface 28, 28A of the tibial platform 24, 24A and porous metal portion 83 of the femoral component 12. In addition, bone ingrowth is also anticipated into the exterior surfaces 70, 72, 76, 79, 70A, 72A, 76A of the extensions 30, 32, 34, 36, 38, 39, 30A, 32A, 34A, 36A, 38A adjacent to the distal surface 28 of the tibial platform 24 and porous metal portion 83 of the femoral component 12 as well as at the junctions 60, 62, 66, 69, 60A, 62A, 66A. Radial pressure along the proximal exterior surfaces 70, 72, 76, 79, 70A, 72A, 76A is expected to be uniform, to stimulate bone ingrowth in all directions on the stem and pegs 30, 32, 34, 36, 38, 39, 30A, 32A, 34A, 36A, 38A. If the free ends 40, 42, 44, 46, 48, 51, 40A, 42A, 44A, 46A of the pegs and stem are smoother (or comprise solid material) than the rest of the porous metal portion, bone is not expected to grow or to grow as vigorously into the smoother exposed exterior surfaces at the free ends 40, 42, 44, 46, 48, 51, 40A, 42A, 44A, 46A of the extensions 30, 32, 34, 36, 38, 39, 30A, 32A, 34A, 36A, 38A.

The extensions 30, 32, 34, 36, 38, 39, 30A, 32A, 34A, 36A, 38A stabilize the implant component 12, 14, 14A when implanted in a bone of a patient. The central stem 30, 30A provides stability against lift off for the tibial tray. The pegs 32, 34, 36, 38, 32A, 34A, 36A, 38A surrounding the central stem 30, 30A and pegs 39 of the femoral component 12 provide stability by reducing shear and micromotion, especially after bone ingrowth has occurred.

If the exposed peripheral surfaces 150, 250 of the implant components are smooth, no soft tissue irritation should occur after the components are implanted and blood should not flow through the porous metal portion into the joint space.

If it later becomes necessary to remove the tibial tray 14, 14A or femoral component 12, the surgeon may cut along the distal bone-engaging surface 28, 28A of the tibial tray platform 24, 24A (or along the distal surface 212 of an augment 200) to sever the connection between the patient's bone and the tibial tray platform 24, 24A at the interface. If the pegs 32, 34, 36, 38, 39, 32A, 34A, 36A, 38A and stem 30, 30A consist of porous metal foam across their entire thicknesses $T_1$ and $T_2$, the surgeon may also cut through all of the extensions 30, 32, 34, 36, 38, 39, 30A, 32A, 34A, 36A, 38A at the junctures 60, 62, 66, 69, 60A, 62A, 66A of the extensions 30, 32, 34, 36, 38, 39, 30A, 32A, 34A, 36A, 38A and the distal surface 28, 28A of the tibial platform 24, 24A and bone-engaging surfaces 13, 15 of the femoral component 12 using a bone saw and easily remove the tibial platform 24, 24A and femoral component 12. Such a result is generally not possible with pegs and stems made of solid titanium or cobalt chrome alloy, since bone saws cannot generally cut through solid metal. To remove the extensions 30, 32, 34, 36, 38, 39, 30A, 32A, 34A, 36A, 38A, the surgeon may then cut around the outer perimeter of each extension 30, 32, 34, 36, 38, 39, 30A, 32A, 34A, 36A, 38A to sever the connection between the bone and the extensions 30, 32, 34, 36, 38, 39, 30A, 32A, 34A, 36A, 38A. Such cuts around the perimeters may be made, for example, through use of a trephine saw. Each extension 30, 32, 34, 36, 38, 39, 30A, 32A, 34A, 36A, 38A may then be readily removed. Notably, if the free ends of the extensions are smooth, little or no bone ingrowth will have occurred at the ends of the extensions, so the removal of the stem and pegs should be made easier.

As indicated above, sawing through the stem and pegs 30, 32, 34, 36, 38, 39, 30A, 32A, 34A, 36A, 38A, 30D, 32D, 36D, 30E, 32E, 36E is made easier if the stem and pegs at the junctions 60, 62, 66, 69, 60A, 62A, 66A, 60D, 62D, 66D, 60E, 62E, 66E consist of porous metal rather than solid metal. Generally, it is believed that the stem and pegs may be cut through transversely with a standard surgical saw if the material is 25-35% of theoretical density. Notably, in the illustrated embodiments, the titanium alloy studs 132, 134, 136, 138, 140, 132A, 134A, 136A, 138A, 140A, 134D, 134E do not extend beyond the plane of bone-engaging surface 28, 28A, 28D, 28E; therefore, in cutting through the extensions 30, 32, 34, 36, 38, 39, 30A, 32A, 34A, 36A, 38A, 30D, 32D, 36D, 30E, 32E, 36E, the surgeon need not cut through the solid metal studs 132, 134, 136, 138, 140, 132A, 134A, 136A, 138A, 140A, 134D, 134E.

It is anticipated that a standard surgical saw could cut through a somewhat more dense material. In addition, it is anticipated that a standard surgical saw could cut through a composite of materials, such as a small diameter central core of solid metal (e.g. titanium alloy) surrounded by a porous metal foam (e.g. commercially pure titanium). Accordingly, although for purposes of ease of removal, it is preferred that the entire thicknesses of the extensions be porous metal at the junctions, other considerations may call for a composite of materials to be used.

Thus, the present invention provides a knee prosthesis with a tibial implant component and femoral component suitable for optimized cementless fixation. Soft tissue irritation and bleed-through may be substantially reduced or eliminated. The strength of a sintered bond between porous and solid metal portions of an implant component may be optimized. Moreover, the implant components may be readily removed from the bone in revision surgery to conserve native bone.

Figure 27:
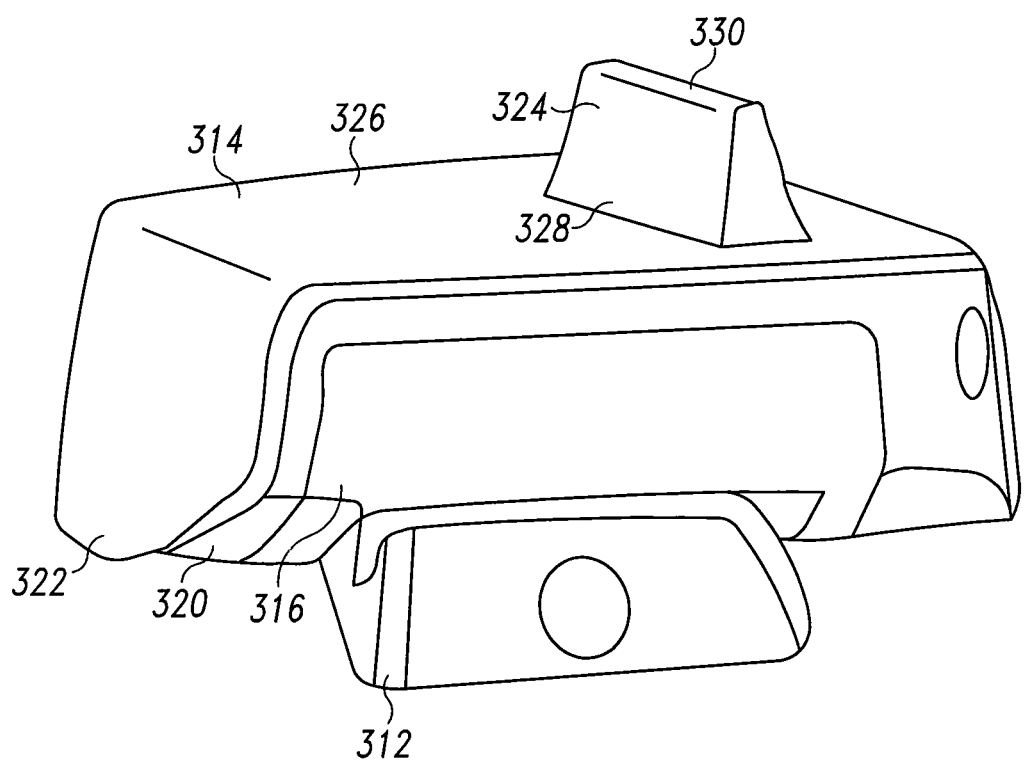
FIG. 27 is a perspective view of an ankle prosthesis embodying the principles of the present invention.

It will be appreciated that the principles of the present invention are expected to be applicable to other joint prostheses as well. An example of such a joint prosthesis is shown in FIG. 27. The joint prosthesis of FIG. 27 is an ankle prosthesis. The illustrated ankle prosthesis comprises a talar component 312, a composite distal tibial component 314 and a bearing 316. In the illustrated embodiment, the composite distal tibial component 314 comprises a distal solid metal portion 320 and a proximal porous metal portion 322, sintered together as described above for the knee prosthesis 10. As in the knee prosthesis 10, the solid metal portion 320 and the bearing may have mounting surfaces with complementary locking features (not shown) so that the bearing 316 can be fixed to the solid metal portion 320 of the tibial component 314. The illustrated distal tibial component 314 has a proximal extension 324 extending proximally from the bone-engaging surface 326 of the tibial component 314. The proximal extension 324 may provide porous metal outer surfaces for engaging the bone or the distal portion 328 may comprise porous metal and the proximal portion 330 comprise porous metal with a porosity or reduced coefficient of static friction as described above. A similar extension could be provided in the talar component if desired.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

For example, the number and configurations of the extensions may be varied. For a tibial tray, for example, the tray could include pegs but no central stem. Although the illustrated tibial trays have four pegs, fewer pegs may be acceptable.

Other variations are possible as well. For example, the extensions 30, 32, 34, 36, 38, 39, 30A, 32A, 34A, 36A, 38A, 30D, 32D, 36D, 30E, 32E, 36E could be made as modular components to be assembled with a base plate intraoperatively if desired. The base plate could comprise a porous preform like that shown in FIG. 8 at 85 sintered to a solid metal portion such as that shown at 80 in FIG. 5. The threaded and Morse taper connections described above should be sufficient to hold the components together without sintering, particularly if the studs are longer, as shown in the embodiment of FIGS. 28-30. The extensions and base plate may be provided in a kit form, with the base plate and extensions being discrete components as shown in FIGS. 8-9 and 17-20; the extensions in the kit could have differing properties, such as size or surface finish, and the surgeon may chose the most appropriate extension for the particular patient intraoperatively. For example, a set of extensions could be provided with porous distal ends and a second set of extensions could be provided with smooth distal ends to accommodate surgeon preference.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. An orthopaedic prosthetic component, comprising:
a polymer modular tibial bearing component, and
a tibial tray component configured to be implanted into a proximal end of a patient's tibia and assembled with the modular tibial bearing intraoperatively, the tibial tray comprising:
a solid metal portion including a proximal-facing surface configured to receive the modular tibial bearing component,
a single, integral metal portion including a porous base having a distal-facing surface positioned opposite the proximal-facing surface, the single, integral portion further including a central stem and a plurality of pegs,
the central stem extending away from the distal-facing surface to a distal tip, the central stem being positioned on a central sagittal plane of the tibial tray component, and
the plurality of pegs being spaced apart from the central stem and extending away from the distal-facing surface, each peg extending to a free distal end that is spaced apart from the central sagittal plane of the tibial tray component,
wherein the porous base has a void space of at least 60% by volume,
wherein each peg includes a porous metal body, a first surface section positioned between the distal-facing surface and its free distal end, and a second surface section positioned distal of the first surface section, and
wherein the first surface section of each peg has a static coefficient of friction, and the second surface section of each peg has a static coefficient of friction that is lower than the static coefficient of friction of the first surface section of the peg.

2. The orthopaedic prosthetic component of claim 1, wherein the second surface section of each peg is positioned at the free distal end of the peg.

3. The orthopaedic prosthetic component of claim 1, wherein each peg includes a solid metal portion coupled to the porous metal body, the solid metal portion including the second surface section of the peg.

4. The orthopaedic prosthetic component of claim 1, wherein the second surface section of each peg includes a smooth outer surface.

5. The orthopaedic prosthetic component of claim 1, wherein:
the central stem includes a porous metal body, a first surface section positioned between the distal-facing surface and its distal tip, and a second surface section positioned distal of the first surface section, and
wherein the first surface section of the central stem has a static coefficient of friction, and the second surface section of the central stem has a static coefficient of friction that is lower than the static coefficient of friction of the first surface section of the central stem.

6. The orthopaedic prosthetic component of claim 5, wherein the second surface section of the central stem is positioned at the distal tip.

7. The orthopaedic prosthetic component of claim 5, wherein the central stem includes a solid metal portion coupled to its porous metal body, the solid metal portion including the second surface section of the central stem.

8. The orthopaedic prosthetic component of claim 5, wherein the second surface section of the central stem includes a smooth outer surface.

9. The orthopaedic prosthetic component of claim 1, wherein:
the tibial tray component further comprising an outer wall extending between the distal-facing surface and the proximal-facing surface,
the solid metal portion includes a proximal section of the outer wall, and
the porous base includes a distal section of the outer wall.

10. An orthopaedic prosthetic component, comprising:
a polymer modular tibial bearing component,
a tibial tray component configured to be implanted into a proximal end of a patient's tibia and assembled with the modular tibial bearing intraoperatively, the tibial tray comprising:
a proximal-facing surface configured to receive the modular tibial bearing component,
a distal-facing surface positioned opposite the proximal-facing surface,
a central stem extending away from the distal-facing surface to a distal tip, the central stem being positioned on a central sagittal plane of the tibial tray component, and
a plurality of pegs spaced apart from the central stem and extending away from the distal-facing surface,
wherein the tibial tray component includes a solid metal portion that includes the proximal-facing surface and a porous metal portion that includes the distal-facing surface and has a void space of at least 60% by volume,
wherein the central stem includes a porous metal body, a first surface section positioned between the distal-facing surface and its distal tip, and a second surface section positioned distal of the first surface section, and
wherein the first surface section of the central stem has a static coefficient of friction, and the second surface section of the central stem has a static coefficient of friction that is lower than the static coefficient of friction of the first surface section of the central stem.

11. The orthopaedic prosthetic component of claim 10, wherein the second surface section of the central stem is positioned at the distal tip.

12. The orthopaedic prosthetic component of claim 10, wherein the central stem includes a solid metal portion coupled to its porous metal body, the solid metal portion including the second surface section of the central stem.

13. The orthopaedic prosthetic component of claim 10, wherein the second surface section of the central stem includes a smooth outer surface.

14. The orthopaedic prosthetic component of claim 10, wherein each peg includes a porous metal body and a solid metal portion coupled to the porous metal body.

15. The orthopaedic prosthetic component of claim 14, wherein the solid metal portion of each peg is positioned at a free distal end of the peg that is spaced apart from the central sagittal plane of the tibial tray component.

16. The orthopaedic prosthetic component of claim 15, wherein the solid metal portion of each peg includes a smooth outer surface.

* * * * *